United States Patent
Anelli et al.

(10) Patent No.: US 10,610,452 B2
(45) Date of Patent: Apr. 7, 2020

(54) CONTAINER CLOSURE OPERATED BY A CONNECTING DEVICE

(71) Applicant: BRACCO IMAGING SPA, Milan (IT)

(72) Inventors: Pier Lucio Anelli, Milan (IT); Cristina Neira, Turin (IT); Andrea Romeo, Milan (IT); Alberto Candotti, Alessandria (IT); Marco Leonardi, Gorgonzola (IT)

(73) Assignee: BRACCO IMAGING SPA, Milan (IT)

( * ) Notice: Subject to any disclaimer, the term of this patent is extended or adjusted under 35 U.S.C. 154(b) by 0 days.

(21) Appl. No.: 16/474,726

(22) PCT Filed: Dec. 18, 2017

(86) PCT No.: PCT/EP2017/083287
§ 371 (c)(1),
(2) Date: Jun. 28, 2019

(87) PCT Pub. No.: WO2018/122019
PCT Pub. Date: Jul. 5, 2018

(65) Prior Publication Data
US 2019/0329943 A1    Oct. 31, 2019

(30) Foreign Application Priority Data

Dec. 29, 2016 (EP) .................................... 16207412

(51) Int. Cl.
*A61J 1/20* (2006.01)
*A61M 39/22* (2006.01)
(Continued)

(52) U.S. Cl.
CPC ............. *A61J 1/2037* (2015.05); *A61J 1/145* (2015.05); *A61J 1/2072* (2015.05); *A61M 39/22* (2013.01);
(Continued)

(58) Field of Classification Search
CPC ........ A61J 1/2037; A61J 1/145; A61J 1/2072; A61M 39/221; A61M 39/22;
(Continued)

(56) References Cited

U.S. PATENT DOCUMENTS 4,324,239 A * 4/1982 Gordon ................ A61M 39/26
251/149.6
4,493,348 A * 1/1985 Lemmons ............. A61J 1/2096
138/109

(Continued)

FOREIGN PATENT DOCUMENTS

| JP | H08244822 A | 9/1996 |
|---|---|---|
| WO | 1998034582 A1 | 8/1998 |

OTHER PUBLICATIONS

PCT Search Report and Written Opinion for PCT/EP2017/083287, dated Apr. 11, 2018.

*Primary Examiner* — James N Smalley
(74) *Attorney, Agent, or Firm* — Vivicar Law, PLLC

(57) ABSTRACT

A solution is proposed for closing a mouth (125) of a container (110) of a liquid (105). A corresponding closure (135) comprises a cap (205) having fixing means (315) for fixing the cap (205) to the container (110), a delivery port (321) for delivering the liquid (105) from the container (110), a valve member (215) in a closed position wherein the valve member (215) closes the delivery port (321), a cap suction conduit (339) for suctioning air into the container (110) during the delivering of the liquid (105) and a connector (327) for connecting to a delivery device (805) of the liquid (105), the connector (327) being in fluid communication with the delivery port (321), a slider (220) slidebly coupled with the cap (205), the slider (220) having a slider suction conduit (440) for suctioning the air into the container (110) during the delivering of the liquid (105) slidebly coupled with the cap suction conduit (339), and a frangible
(Continued)

element (345) closing the cap suction conduit (339) or the slider suction conduit (440), wherein the closure (135) is configured to cause the delivery device (805) during the connecting thereof to move inwards the container (110), in a fixed condition wherein the closure (135) is fixed to the container (110), and thus moving the valve member (215) inwards the container to an open position, wherein the valve member (215) opens the delivery port (321), and moving the slider (220) inwards the container to break the frangible element (345), thereby putting in fluid communication the slider suction conduit (440) with the cap suction conduit (339).

15 Claims, 12 Drawing Sheets

(51) Int. Cl.
  *B65D 47/24* (2006.01)
  *B65D 47/36* (2006.01)
  *A61J 1/14* (2006.01)
  *A61M 39/24* (2006.01)
  *A61M 39/20* (2006.01)

(52) U.S. Cl.
  CPC ............ *A61M 39/221* (2013.01); *B65D 47/24* (2013.01); *B65D 47/36* (2013.01); *A61M 2039/205* (2013.01); *A61M 2039/2486* (2013.01); *B65D 2205/025* (2013.01)

(58) Field of Classification Search
  CPC .... A61M 2039/205; A61M 2039/2486; B65D 47/36; B65D 47/24; B65D 2205/025
  USPC ........ 215/247, 249, 308, 309; 604/256, 415; 220/254.9
  See application file for complete search history.

(56) References Cited

U.S. PATENT DOCUMENTS

| | | | |
|---|---|---|---|
| 5,620,434 A * | 4/1997 | Brony | A61J 1/2096 141/320 |
| 5,702,019 A * | 12/1997 | Grimard | A61J 1/2096 141/24 |
| 5,713,493 A | 2/1998 | Garibaldi | |
| 5,848,994 A | 12/1998 | Richmond | |
| 6,997,917 B2 * | 2/2006 | Niedospial, Jr. | A61J 1/2096 206/828 |
| 8,016,143 B2 * | 9/2011 | Perrin | B29C 45/4407 215/253 |
| 9,849,067 B2 * | 12/2017 | Vassallo | B65D 47/0804 |
| 2002/0066715 A1 * | 6/2002 | Niedospial, Jr. | A61J 1/2096 604/415 |
| 2003/0127467 A1 | 7/2003 | Adams et al. | |
| 2011/0054436 A1 * | 3/2011 | Griffis, III | A61J 1/2096 604/407 |
| 2011/0168292 A1 | 7/2011 | Luzbetak et al. | |
| 2012/0103470 A1 * | 5/2012 | Terwilliger | A61J 1/2096 141/346 |

* cited by examiner

CONTAINER CLOSURE OPERATED BY A CONNECTING DEVICE

CROSS-REFERENCE TO RELATED APPLICATIONS

This application is the national stage application of corresponding international application number PCT/EP2017/083287, filed Dec. 18, 2017, which claims priority to and the benefit of European application no. 16207412.4, filed Dec. 29, 2016, all of which are hereby incorporated by reference in their entirety.

TECHNICAL FIELD

The present disclosure relates to the field of containers for liquids. More specifically, the disclosure relates to closures for these containers.

BACKGROUND ART

The background of the present disclosure is hereinafter introduced with the discussion of techniques relating to its context. However, even when this discussion refers to documents, acts, artifacts and the like, it does not suggest or represent that the discussed techniques are part of the prior art or are common general knowledge in the field relevant to the present disclosure.

Containers of impervious material (for example, glass) are commonly used to store liquids in a number of applications. Particularly, in medical applications the containers store medical liquids to be administered to patients; for example, in hospital environments these containers are commonplace for storing contrast agents that are to be injected into the patients (such as by an automated injection system during scan examinations thereof).

Most containers have a mouth (i.e., an opening) for loading and delivering the liquid; a typical example is a bottle, i.e., a rigid container having a larger body with a neck ending with the mouth. Each container of this type is provided with a closure, which closes the container to avoid losing the liquid and to protect the liquid from environment contamination (before its use).

A widespread type of closure is based on a membrane that seals the mouth of the container. In this case, a spike (for example, a needle) is commonly used to pierce the membrane for extracting the liquid from the container through it (with the container that remains substantially closed even when the spike is removed after the administration of the liquid). However, any accidental contacts with the spike may contaminate it and then the liquid when the spike is inserted into the container, with a consequent final possible contamination of the patient. Moreover, the spike is quite hazardous and it may cause injuries to a corresponding operator, with the risk of transmitting diseases as well.

Alternatively, the closure may be provided with an internal spike (which is not accessible from the outside). In this case, when a delivery device is coupled with the closure (for example, by screwing a luer lock fitting), the delivery device pushes the spike that pierces the membrane analogously to the previous technique.

In any case, the piercing of the membrane by the spike (either internally or externally to the closure) may cause the detachment of particles of the membrane and their falling within the container, with the risk of contamination of the liquid stored in the container.

Closures that do not require any spike for delivering the liquid (i.e., of the spike-less type) have also been proposed. For example, a closure of this type may be provided with a valve member that closes a delivery port of the liquid. When the delivery device is coupled with the closure of the container, the delivery device pushes the valve member inwards the container, thereby opening the delivery port that allows the liquid to flow from the container to the delivery device. The delivery port of the closure may also be sealed by a frangible element, which is broken by the valve member when it opens the delivery port.

Moreover, the closure may be provided with an elastic element associated with the valve member. According to this technique, the delivery device pushes the valve member to open the delivery port in opposition to the elastic element; therefore, when the delivery device is removed (after the administration of the liquid) the elastic element moves back the valve member so as to close the delivery port again.

In addition, as mentioned in WO-A-98/34582, the closure may have an air release valve to allow air to flow into the container as the liquid is delivered. As described in US-A-2011/0168292, the closure may also have one or more air-release openings, or vents, which are provided with an umbrella valve, with a long tube and a short tube or with a self-sealing valve; the air-release openings are sealed by a microhole covering, which is a semi-permeable membrane that allows air to enter or to exit but it does not permit the passage of liquids.

However, none of the closures known in the art is completely satisfactory under several points of view. For example, improvements would be desirable with respect to structure, assembling, usage and safety of the closures.

SUMMARY

A simplified summary of the present disclosure is herein presented in order to provide a basic understanding thereof; however, the sole purpose of this summary is to introduce some concepts of the disclosure in a simplified form as a prelude to its following more detailed description, and it is not to be interpreted as an identification of its key elements nor as a delineation of its scope.

In general terms, the present disclosure is based on the idea of providing a valve member closing a delivery port for delivering a liquid from a container and a frangible element closing a suction conduit for suctioning air into the container.

Particularly, an aspect provides a closure (for closing a mouth of a container of a liquid) that comprises a valve member closing a delivery port for delivering the liquid and a frangible element closing a suction conduit for suctioning air into the container, wherein the closure is configured to cause a delivery device (during a connecting thereof to a connector of the closure) to move the valve member to open the delivery port and to move a slider to break the frangible element.

A further aspect provides a product containing this closure.

A further aspect provides a method for assembling the closure.

A further aspect provides a method for manufacturing the product.

A further aspect provides a method for using the product.

More specifically, one or more aspects of the present disclosure are set out in the independent claims and advantageous features thereof are set out in the dependent claims, with the wording of all the claims that is herein incorporated verbatim by reference (with any advantageous feature provided with reference to any specific aspect that applies mutatis mutandis to every other aspect).

BRIEF DESCRIPTION OF THE DRAWINGS

The solution of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes—such as value, content and representation). In this respect, it is expressly intended that the figures are not necessary drawn to scale (with some details that may be exaggerated and/or simplified) and that, unless otherwise indicated, they are merely used to illustrate the structures and procedures described herein conceptually. Particularly.

DETAILED DESCRIPTION

Figure 1:
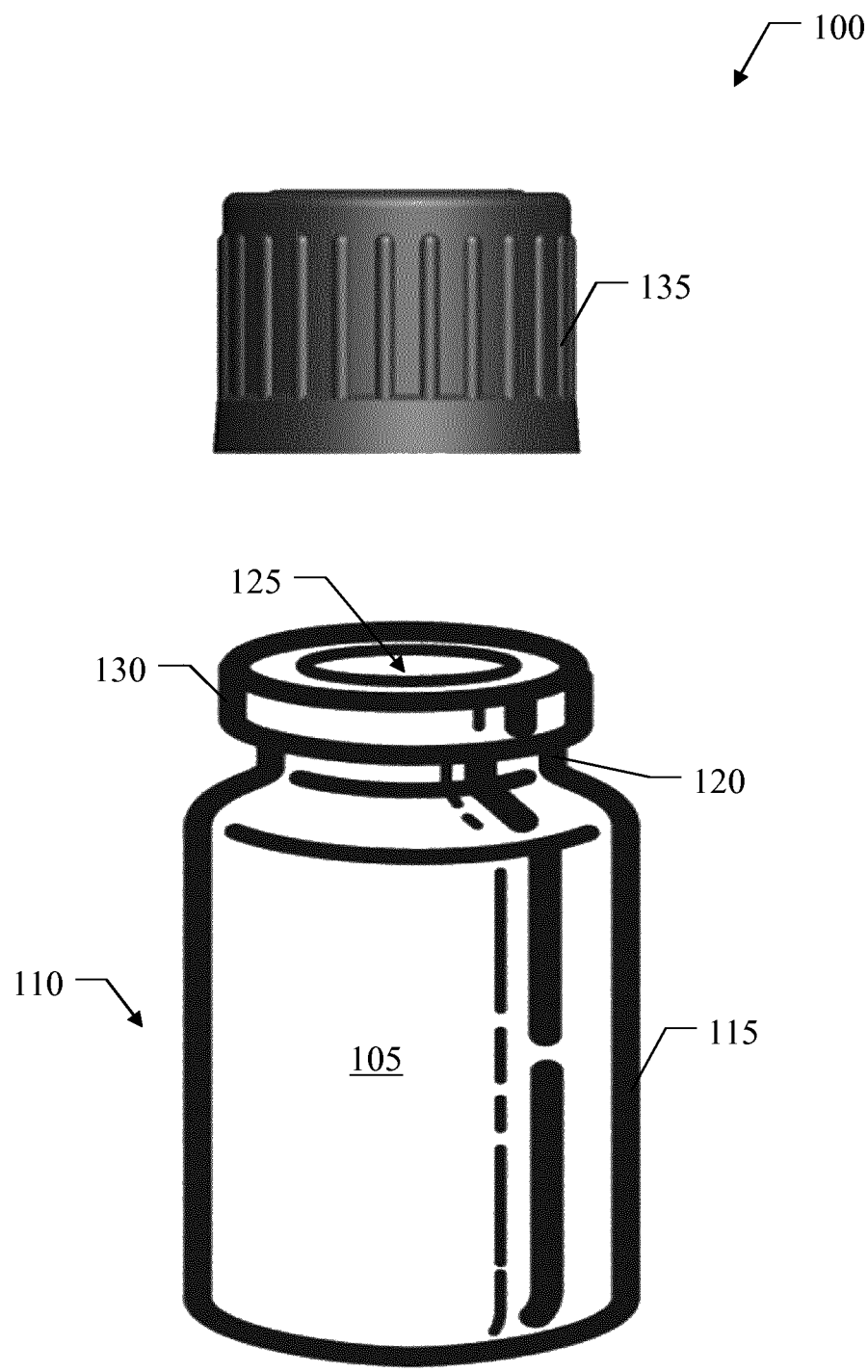
FIG. 1 shows a schematic expanded view of a medical product wherein the solution according to an embodiment of the present disclosure may be applied.

With reference in particular to FIG. 1, a schematic exploded view is shown of a medical product 100 wherein the solution according to an embodiment of the present disclosure may be applied.

The medical product 100 is an artifact for use in medical applications (for example, in hospitals). The medical product 100 contains a medical liquid 105 to be administered to a patient, for example, a contrast agent (such as ISOVUE by Bracco Diagnostics Inc., trademarks) to be injected into the patient by an (automated) injection system during a scan examination of the patient (such as a CT, MR or ultrasound imaging procedure). The medical product 100 comprises a container 110 (for example, a bottle) that stores the medical liquid 105 (such as with a capacity from 50 to 500 ml). The container 110 is made of an impervious material for containing the medical liquid 105 (for example, glass), which is substantially rigid (i.e., maintaining its shape in normal conditions of use). The container 110 has a main body 115 (for example, of a generic cylindrical shape), which is filled (at least in part) with the medical liquid 105. At one axial extremity thereof, the main body 115 narrows into a neck 120 ending with a (circular) mouth 125, which is used to load the medical liquid 105 into the container 110 and to deliver the medical liquid 105 from it. The mouth 125 is encircled by an (out-turned) rim 130.

As described in detail in the following, the medical product 100 comprises a closure 135 (for example, of plastic material). The closure 135 is fixed to the container 110 for closing its mouth 125 (to prevent losing the medical liquid 105 and to protect it from environment contamination before use); at the same time, the closure 135 allows delivering the medical liquid 105, for example, to a (spike-less) delivery device (not shown in the figure), such as a transfer set of the injection system.

Figure 2:
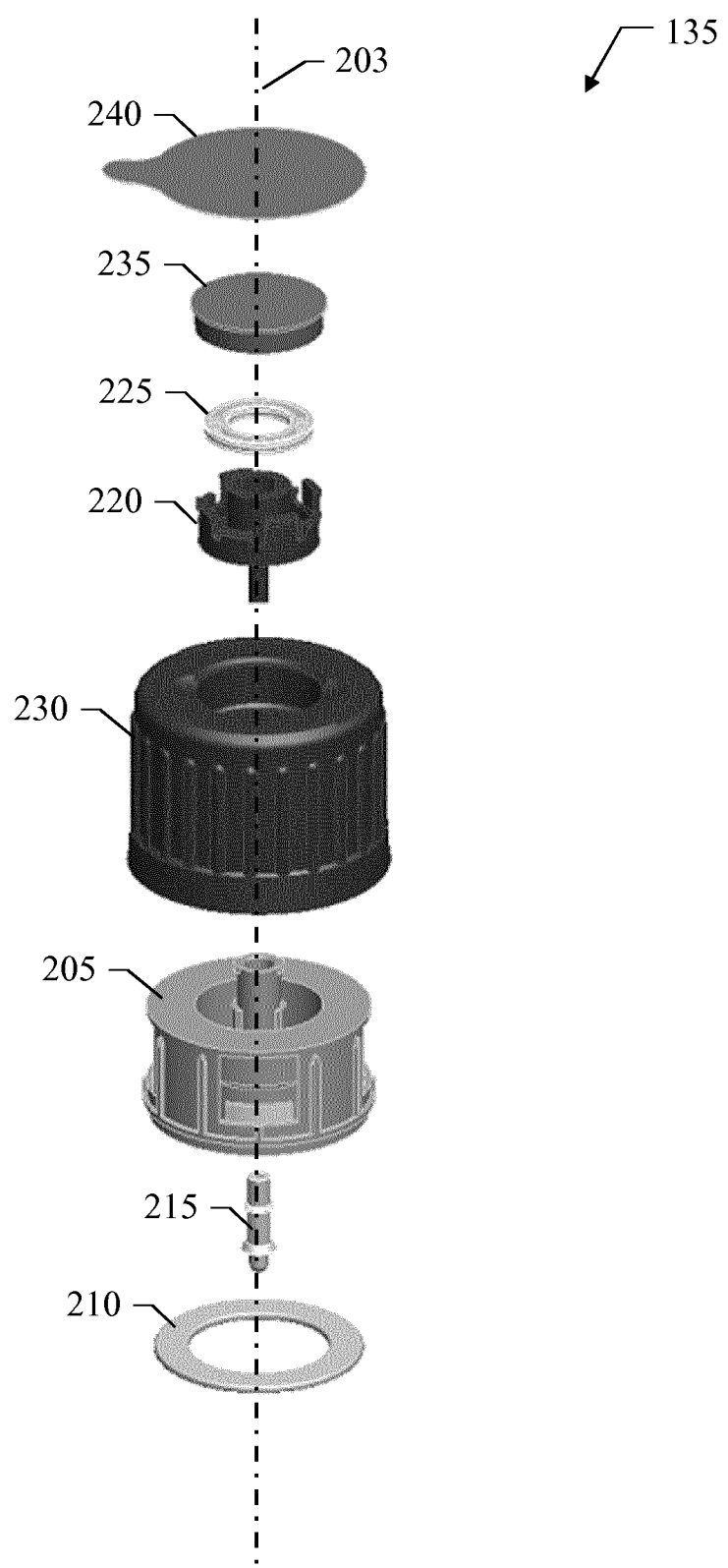
FIG. 2 shows a schematic exploded view of a closure according to an embodiment of the present disclosure.

With reference now to FIG. 2, a schematic exploded view is shown of the closure 135 according to an embodiment of the present disclosure.

The closure 135 comprises the following components (exploded along a longitudinal axis 203 of the closure 135). A cap 205 is used to fix the closure 135 to the container for closing its mouth (not shown in the figure). A gasket 210 is used to seal a coupling between the container and the cap 205 (to prevent any leakage of the medical liquid). A valve member 215 is used to control the delivery of the medical liquid from the container.

In the solution according to an embodiment of the present disclosure, as described in detail in the following, a slider 220 is provided. When the delivery device (not shown in the figure) is connected to the closure 135 in a condition of use, the delivery device moves the valve member 215 to open it, so as to enable the delivery of the medical liquid; at the same time, the delivery device moves the slider 220 to break a frangible element (not shown in the figure), so as to enable the suction of air from the external environment into the container as the medical liquid is delivered out of the container.

The above-described solution is very effective under several points of views.

Particularly, the closure has a spike-less structure that avoids any risk of contaminations and injuries typically correlated to the presence of a spike. Moreover, the suction of the air into the container significantly improves the flow of the medical liquid.

Particularly, this result is achieved by exploiting the valve member (for the medical liquid) and the frangible element (for the air). Therefore, the valve member allows controlling the delivery of the medical liquid with a structure that is very easy to manufacture; at the same time, the frangible element allows maintaining the container closed before use (preventing the suctioning of the air) with a structure that is very simple and of limited dimensions.

The closure of the present disclosure already contains all the components that are necessary for the correct operation thereof. This means that the medical product provided with it is ready to be used, as well as very safe and easy for an operator to manage and work (for example, there is no need of any additional needle for accessing the inside of the container).

In view of the above, the use of the medical product provided with this closure is very easy. Particularly, the opening of the valve member and the breaking of the frangible element is obtained automatically during the connection of the delivery device to the closure and then it does not require any additional (dedicated) operation.

Moreover, a filter 225 is used to filter the air that is suctioned into the container. A cover 230 is used to cover the above-mentioned components 205-225 of the closure 135 (to prevent access to the fixing of the cap 205 to the container, to protect the components 205-225 from the external environment and to provide a good grip to the operator acting on the closure 135 at the same time preventing breakage of gloves usually worn by him/her). A lid 235 is used to close an opening of the cover 230 (to protect the components exposed through it before use and to avoid losing any residual medical liquid after use). A protection film 240 is used to complete a sealing of the cover 230 (to prevent contamination and to ensure integrity of the medical product 100 before use).

Figure 3:
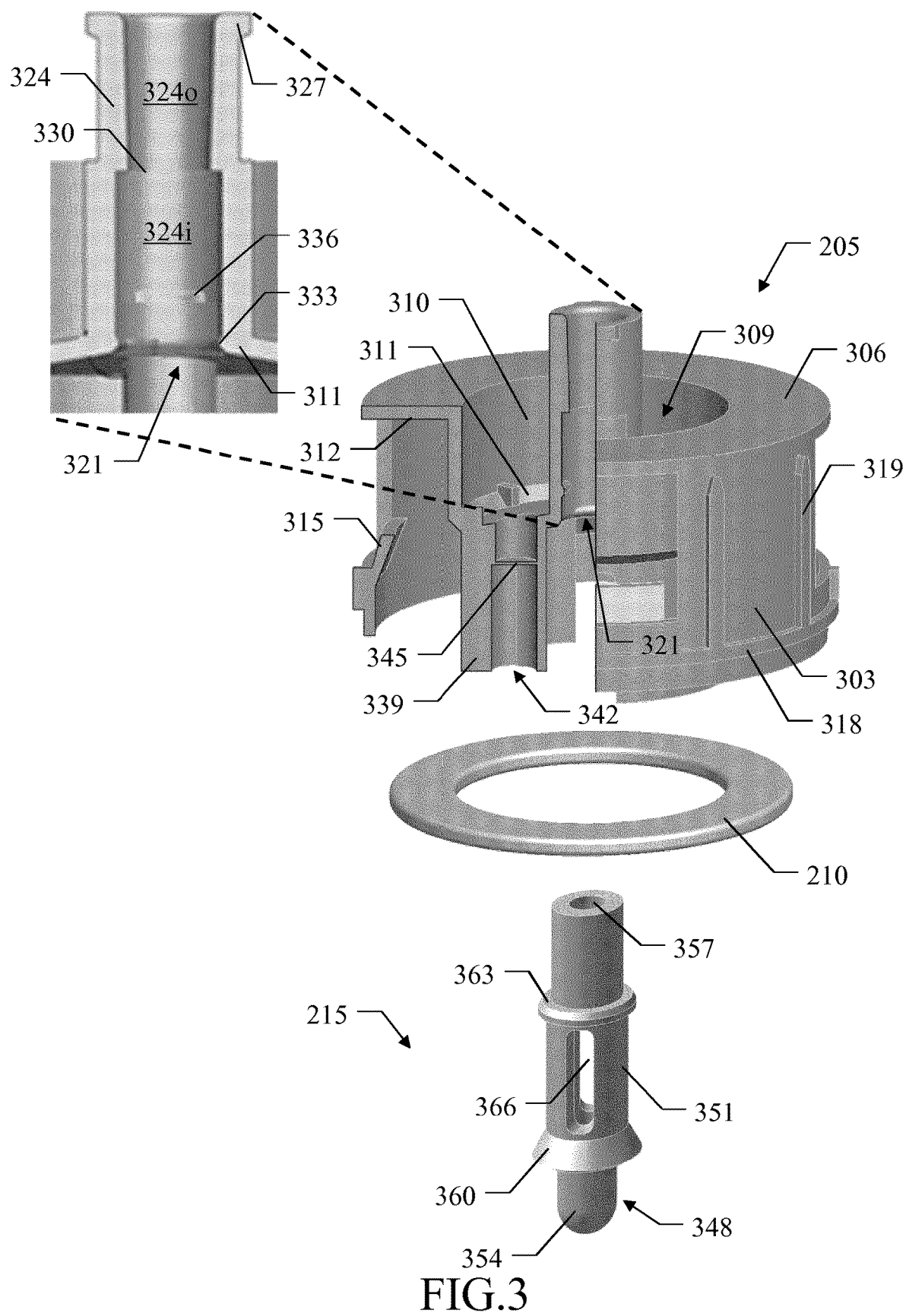
FIG. 3-FIG. 5 show schematic exploded views of some components of the closure according to an embodiment of the present disclosure.
Figure 4:
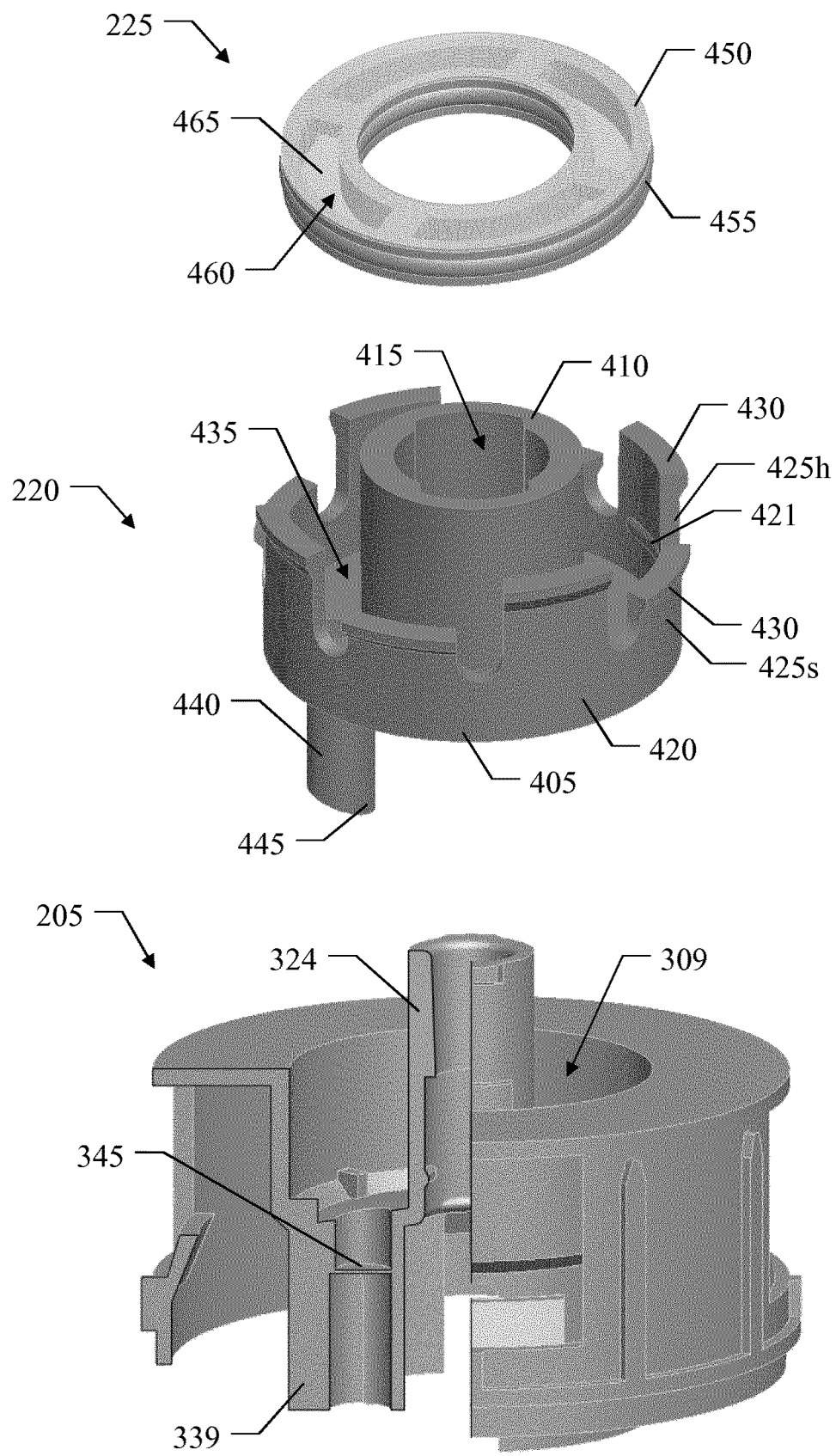
Figure 5:
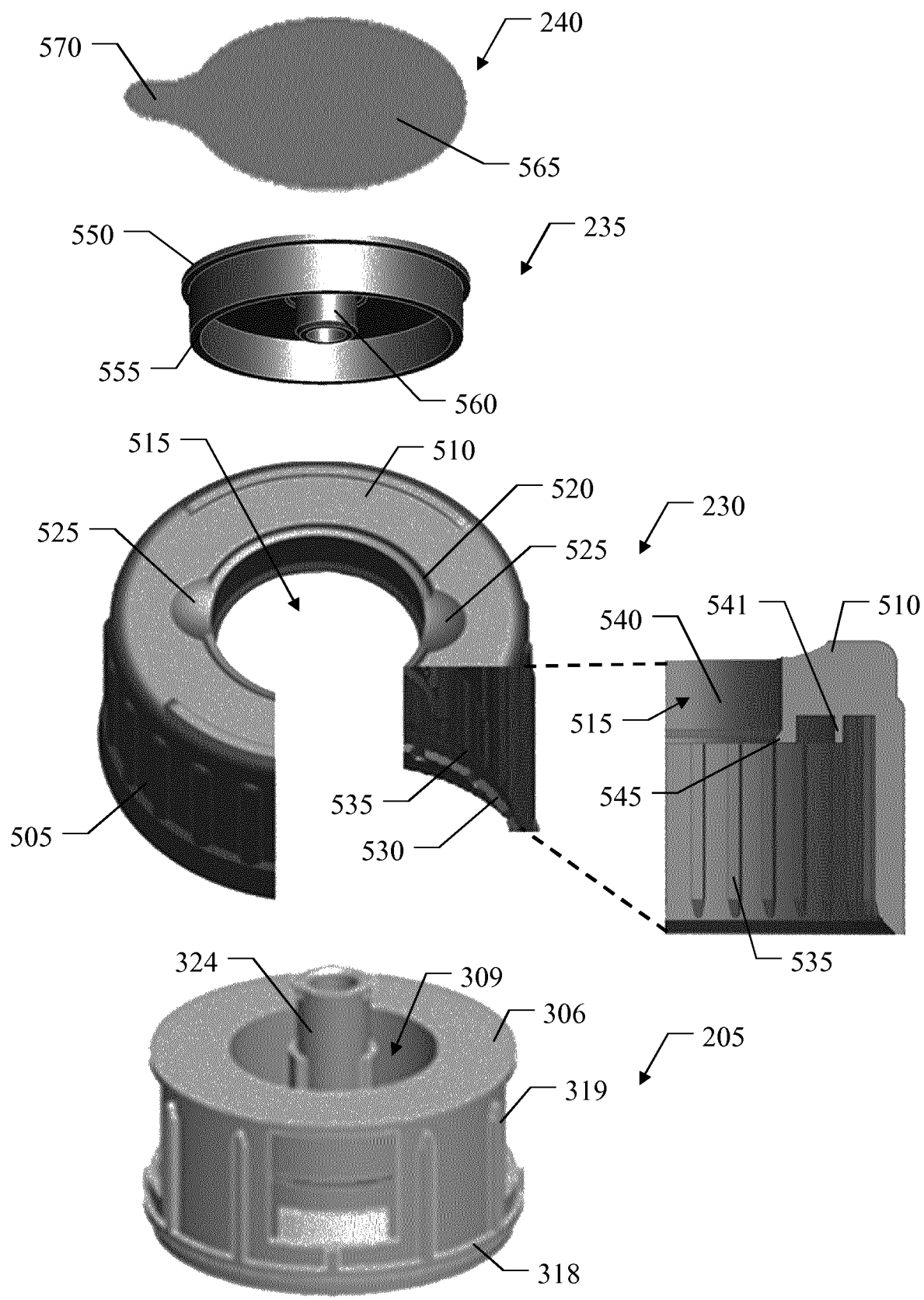

With reference now to FIG. 3-FIG. 5, schematic exploded views are shown of some components of the closure according to an embodiment of the present disclosure.

Starting from FIG. 3, the cap 205 (shown in partially cut-away view) is a body (for example, made from polypropylene homopolymer, PPH) with a generic hollow cylindrical shape (matching the neck of the container, not shown in the figure), which is defined by a lateral wall 303 closed at the top (facing outwards the container in a fixed condition, wherein the closure is fixed to the container) by a disk 306 (whereas it is open at the opposite end thereof, i.e., at the bottom). The disk 306 has a central depression 309 for housing the slider, not shown in the figure (with a depth lower than a height of the lateral surface 303); the depression 309 is delimited by a lateral wall 310 and a bottom wall 311. A region inside the cap 205 close to the disk 306 (between the lateral wall 303 and the lateral wall 310), with the addition of an undercut that is formed inside the lateral wall 303 (not shown in the figure), defines a seat 312 for housing the gasket 210 (wherein some bumps, not shown in the figure, are provided on the internal surface of the lateral wall 303 for interfering therewith). One or more teeth 315 (for example, from 4 to 8) project inwards from the lateral wall 303, slightly inside a free border thereof, for fixing to the container; the teeth 315 extend obliquely, towards the inside of the cap 205 (i.e., towards the disk 306). A rim 318 projects outwards from the lateral wall 303 close to its free border for fixing the cover (not shown in the figure). A plurality of ribs 319 (for example, from 5 to 10) project outwards from the lateral wall 303, longitudinally along it, for interfering rotationally with the cover.

As better visible in a corresponding enlarged portion of the cap 205, a delivery port 321 is open at the center of the bottom wall 311 for delivering the medical liquid from the container; the delivery port 321 has a size corresponding to a desired flow rate of the medical liquid (for example, it has a cross-section from 10 to 40 mm$^2$). A delivery conduit 324 extends upwards (outwards in the fixed condition) from the delivery port 321; the delivery conduit 324 is higher than the depth of the depression 309, so that a portion of the delivery conduit 324 projects above (outside in the fixed condition) the disk 306. An axial free end of the delivery conduit 324 (projecting above the disk 306) is configured as a connector 327 for matching with the delivery device (not shown in the figure), to be connected thereto for delivering the medical fluid from the container. For example, the connector 327 is a female luer lock fitting comprising a tabbed hub with an external thread for engaging with a male luer lock fitting of the delivery device. The delivery conduit 324 has a lower (inner in the fixed condition) portion 324$i$ that is larger (matching a central portion of the valve member 215) and an upper (outer in the fixed condition) portion 324$o$ that is narrower and slightly tapered (matching a corresponding end portion of the valve member 215), so that a connection surface thereof defines an internal shoulder 330 for stopping the valve member 215. One or more humps 333 (for example, from 2 to 4) project inwards the delivery conduit 324 at the delivery port 321 for interfering with the valve member 215. One or more steps 336 (for example, from 2 to 4) project inwards the delivery conduit 324 at a short distance from the delivery port 321 (for example, 0.5-2.0 mm) for interfering with the valve member 215 as well.

Referring back to the overall representation of the cap 205, a first suction conduit, referred to as cap suction conduit 339, extends downwards (inwards in the fixed condition) from the periphery of the bottom wall 311 (up to the free border of the lateral wall 303). The cap suction conduit 339 ends with a suction port 342 (distal from the bottom wall 311) for suctioning air from the external environment into the container during the delivery of the medical liquid. As a result, the suction port 342 is spaced apart longitudinally from the delivery port 321 by the length of the cap suction conduit 339 (for example, by 4-12 mm, preferably by 5-10 mm and still more preferably by 6-8 mm, such as by 7 mm), so that in the fixed condition the suction port 342 is positioned more in depth within the container (and thus more far away from the mouth of the container) than the delivery port 321. The size of the suction port 342 is designed in order to obtain the desired flow rate of the medical liquid to be delivered through the delivery conduit 324.

Generally, the delivery port 321 and the suction port 342 differ structurally (in addition to for their use). Particularly, the suction port 342 is smaller in cross-section area than the delivery port 321 (for example, the cross-section area of the suction port 342 is about 25-75% of the cross-section area of the delivery port 321). The delivery port 321 is in fluid communication with the connector 327, whereas no connector is generally required for the suction port 342. Moreover, the suction port 342 is coupled with the filter (not shown in the figure), whereas no filter is generally required for the delivery port 321.

A frangible element 345 (i.e., an element which may be broken relatively easily, instead of deforming) closes the cap suction conduit 339 (and then the suction port 342 as well). For example, the frangible element 345 is a membrane that is attached through its border to an internal wall of the cap suction conduit 339 at a predetermined height thereof. Preferably, the membrane has pre-cut lines, extending along a substantial portion of the circumference thereof, which facilitate its breaking without losing parts inside the container (and thus in the medical liquid) and without detaching from the internal wall of the cap suction conduit 339.

The gasket 210 is an O-ring with a generic toroidal shape (for example, made from styrene ethylene butylene styrene copolymer, SEBS) matching the seat 312 of the cap 205.

The valve member 215 (for example, made from PPH or Polyamide (Nylon) 11, PA11) comprises a tube 348, with a lateral wall 351, a closed end 354 with an ogive shape facing downwards (inwards in the fixed condition) and an open end 357 facing upwards (outwards in the fixed condition). A skirt 360 projects outwards from the lateral wall 351 near the closed end 354. The skirt 360 extends obliquely from the lateral wall 351, towards the closed end 354. A rim 363 extends radially (i.e., substantially transversally) from the lateral wall 351 near the open end 357. An (upper) portion of the valve member 215, i.e., the portion from the rim 363 to the open end 357, matches in width the outer portion 324$o$ of the delivery conduit 324 but it is shorter (for example, the length of the upper portion is from 5 to 10 mm). A (central) portion of the valve member 215, i.e., the portion comprised between the rim 363 and the skirt 360 and including both the rim 363 and the skirt 360, substantially matches the inner portion 324$i$ of the delivery conduit 324 (both in width and in height). An external diameter of the rim 363 is slightly lower than an internal diameter of the inner portion 324$i$ of the delivery conduit 324 and of an inner radial extent of the steps 336), but it is considerably higher (for example, by at least from 0.5 to 2 mm) than an internal diameter of the outer portion 324o of the delivery conduit 324 for interfering with the internal shoulder 330. Moreover, an external diameter of the skirt 360 is higher than an internal diameter of the delivery port 321 and of an inner radial extent of the humps 333 for interfering therewith. One or more windows 366 (for example, from 2 to 4) are provided in the lateral wall 351 between the skirt 360 and the rim 363 (for the passage of the medical liquid from the container to the open end 357 during use).

Moving to FIG. 4, the slider 220 is a body (for example, made from cyclic olefin copolymer, COC, cyclic olefin polymer, COP or polypropylene carbonate, PC) with a generic cylindrical shape matching the depression 309 of the cap 205. Particularly, the slider comprises a disk 405 matching in width the depression 309. A turret 410 extends upwards (outwards in the fixed condition) from a center of the disk 405; the turret 410 is hollow, with a through-hole 415 matching in width the delivery conduit 324 and matching in height the depression 309 (therefore the turret 410 is shorter than the delivery conduit 324). A crown 420 with a crenellated profile extends upwards (outwards in the fixed condition) from a peripheral border of the disk 405. Particularly, the crown 420 defines a plurality of tabs with different heights, for example, alternated to each other. Some of the tabs are higher tabs 425h matching in height the depression 309 and some of the tabs are lower tabs 425s shorter than the higher tabs 425h (for example, the height of the lower tabs 425s is from 30 to 60% the height of the higher tabs 425h). All the (higher and lower) tabs 425h, 425s end with a tooth 430 projecting radially outwards for interfering with the cover (not shown in the figure). A region inside the slider 220 close to the disk 405 (i.e., comprised between the turret 410 and the crown 420) defines a seat 435 for receiving the filter 225. One or more bumps 421 project inwards from the crown 420 in proximity of the seat 435 for interfering with the filter 225. A second suction conduit, referred to as slider suction conduit 440, extends downwards (inwards in the fixed condition) from the disk 405 (i.e., the slider suction conduit 440 originates from the region comprised between the turret 410 and the crown 420). An external diameter of the slider suction conduit 440 matches an internal diameter of the cap suction conduit 339 for sliding therein (whereas the slider suction conduit 440 is shorter than the cap suction conduit 339). An axial free (lower) end of the slider suction conduit 440 (distal from the disk 405) is slanted so as to define a sharpened tip 445 for acting on the frangible element 345.

The filter 225 comprises a support ring 450 (for example, made from polypropilene, PP, or acrylonitrile butadiene styrene, ABS) matching the seat 435 of the slider 220; the support ring 450 has a bulging lateral wall 455 (with a convex profile) for interfering with an internal wall of the crown 420 of the slider 220. One or more windows 460 (for example, from 2 to 8) are provided in the support ring 450. The support ring 450 holds an anti-bacterial membrane 465, which is exposed in the windows 460. The anti-bacterial membrane 465 exposed in the windows 460 is larger than a cross-section of the slider suction conduit 440 of the slider 220.

Moving to FIG. 5, the cover 230 (shown in partially cut-away view) is a body (for example, made from polypropilene, PP) with a generic hollow cylindrical shape (matching the cap 205), which is defined by a lateral wall 505 that is closed at the top (externally in the fixed condition) by a disk 510 (whereas it is open at the opposite end thereof, i.e., at the bottom). The disk 510 has a central through-hole 515; the through-hole 515 has a diameter matching a diameter of the depression 309 of the cap 205. A counterbore 520 is formed around the through-hole 515 for receiving the lid 235. One or more access dips 525 are provided outside the disk 510 starting from the counterbore 520 for pulling the lid 235. A ring with one or more teeth 530 (for example, from 4 to 8) project inwards from the lateral wall 505, slightly inside a free border thereof, for interfering with the rim 318 of the cap 205; the teeth 530 extend obliquely, towards the inside of the cover 230. A plurality of ribs 535 project inwards from the lateral wall 505, longitudinally along it, for engaging with the ribs 319 of the cap 205 (for example, with one rib 319 of the cap 205 every 2-4 ribs 535 of the cover 230). As better visible in a corresponding enlarged portion of the cover 230, a crown 540 extends downwards (inwards in the fixed condition) from a border of the through-hole 515 and another crown 541 extends downwards from the disk 510 around the crown 540; the crowns 540,541 have a height corresponding to the portion of the delivery conduit 324 projecting upwards (outside in the fixed condition) the disk 306 of the cap 205. The crown 540 ends with an in-turned lip 545, i.e., the lip 545 protrudes in a radial direction inwards the through-hole 515, for interacting with the tabs of the slider (not shown in the figure).

The lid 235 (for example, made from polypropylene, PP, or a thermoplastic elastomer) comprises a disk 550, which matches in width and in height the counterbore 520. A crown 555 extends downwards (inwards in the fixed condition), starting slightly inside a border of the disk 550. The crown 555 is remarkably shorter than the crown 540; the crown 555 has an external diameter matching an internal diameter of the crown 540. A (hollow) turret 560 extends downwards (inwards in the fixed condition) from a center of the disk 550; the turret 560 has a height equal to (or slightly lower than) a height of the crown 555 and an external diameter matching an internal diameter of the delivery conduit 324 of the cap 205.

The protection film 240 (for example, made from aluminum) comprises a circular body 565 (slightly larger than the through-hole 515), with a handling tab 570 projecting laterally from it.

With reference now to FIG. 6A-FIG. 6E, the main steps are shown of a process for assembling the closure according to an embodiment of the present disclosure.

Figure 6A:
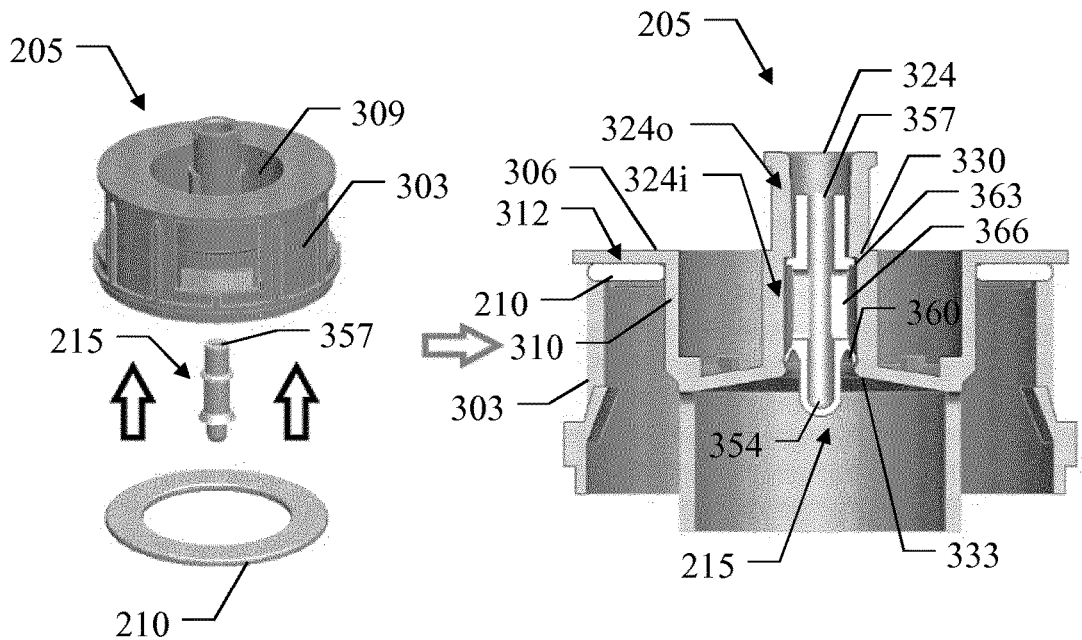
FIG. 6A-FIG. 6E show the main steps of a process for assembling the closure according to an embodiment of the present disclosure.

Starting from FIG. 6A, the gasket 210 is mounted into the cap 205 by pushing it (from below, as indicated by the arrows) between the lateral wall 303 and the lateral wall 310 of the cap 205. The gasket 210 is pushed until it abuts against the lower surface of the disk 306. At this point, the gasket 210 is blocked into the seat 312 by means of the bumps (not shown in the figure) that are provided on the internal surface of the lateral wall 303. Moreover, the valve member 215 is snap fitted into the cap 205 by pushing it (from below, as indicated by the arrows) into the delivery conduit 324, with its open end 357 forward-facing (upwards). The rim 363 of the valve member 215 overcomes the humps 333 and the steps (not shown in the figure) of the delivery conduit 324 thanks to a chamfered edge thereof and to its resilient yielding (then the rim 363 returns elastically to its original shape as soon as these obstacles have been overcome). Moreover, when the skirt 360 reaches the humps 333, the orientation of the skirt 360 (towards the closed end 354) and its resilient yielding allow the skirt 360 to overcome the humps 333 (then the skirt 360 returns elastically to its original position as soon as this obstacle has been overcome). The valve member 215 is pushed until its rim 363 abuts against the internal shoulder 330 of the delivery conduit 324. As a result, the valve member 215 is brought to a closed position. Particularly, the (inner) portion of the valve member 215, i.e., the portion from the rim 363 to the open end 357, projects into the outer portion 324o of the delivery conduit 324, with the open end 357 that remains within the delivery conduit 324 and spaced apart from the free end of the delivery conduit 324. At the same time, the (central) portion of the valve member 215, i.e., the portion from the rim 363 to the skirt 360 comprising the windows 366, is located inside the inner portion 324i of the delivery conduit 324. The interference of the skirt 360 with the humps 333 retains the valve member 215 in place during the next handling of the cap 205; moreover, the skirt 360 is pressed within the delivery conduit 324 (thanks to their interference), so as to seal it (with the sealing that is amplified by the above-mentioned interference of the skirt 360 with the humps 333).

Figure 6B:
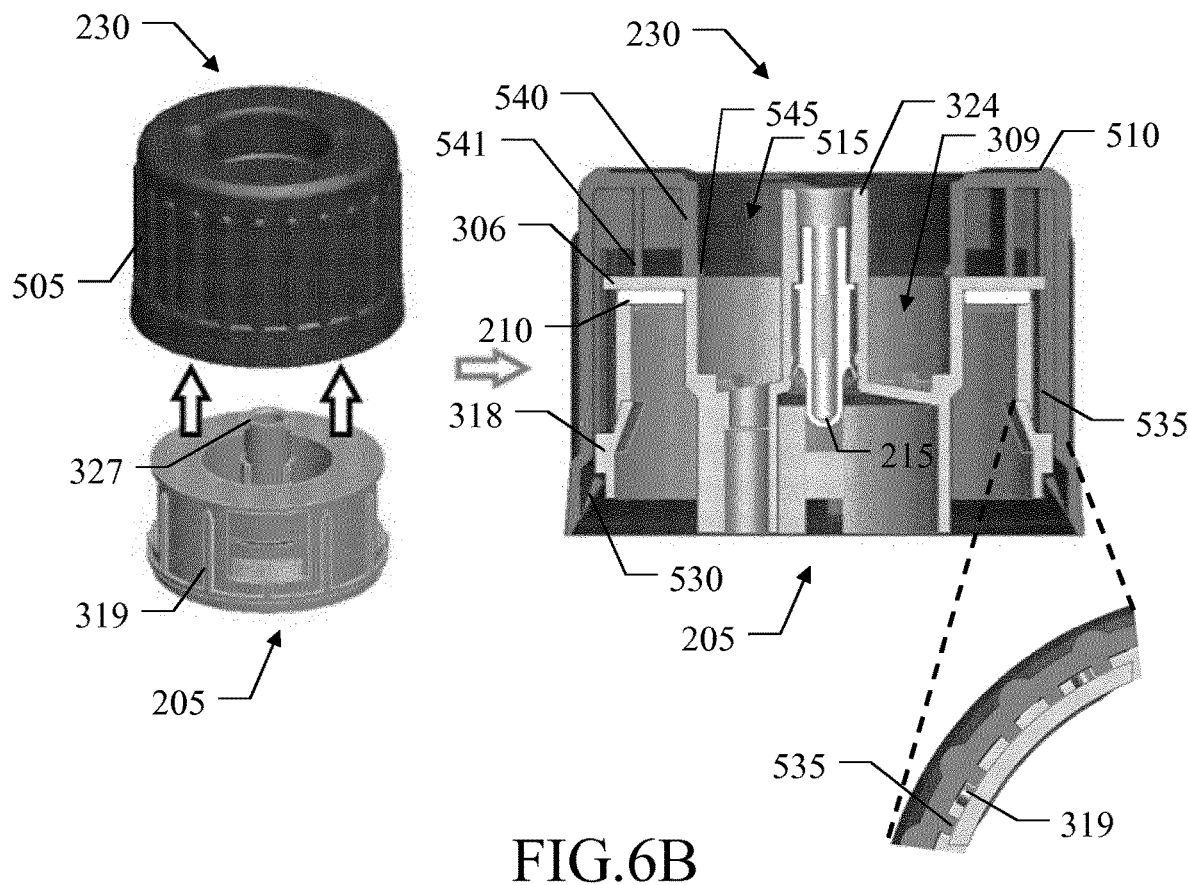

Moving to FIG. 6B, the cap 205 (already provided with the gasket 210 and the valve member 215) is snap fitted into the cover 230 by pushing it (from below, as indicated by the arrows) within the lateral wall 505, with the connector 327 forward-facing (upwards). As better visible in a corresponding enlarged portion of the cap 205 and the cover 230, they are pre-oriented so that the corresponding ribs 319 and 535 are staggered. When during this operation the teeth 530 of the cover 230 are reached by the rim 318 of the cap 205, the orientation of the teeth 530 towards the inside of the cover 230 causes their resilient yielding, thereby allowing the passage of the rim 318 and the final engagement of the cover 230 onto the cap 205 (with the teeth 530 that then return elastically to their original position). The cap 205 is pushed until its disk 306 abuts against the crowns 540,541 of the cover 230 (with its lip 545 slightly projecting within the depression 309), thereby having the delivery conduit 324 projecting into the through-hole 515 (slightly below the level of the disk 510). As a result, the interlocking of the teeth 530 with the rim 318 fixes together the cover 230 and the cap 205; moreover, since the teeth 530 are not accessible from the outside of the cover 230 when the closure is mounted on the container (not shown in the figure), the fixing is non-reversible (i.e., it is not possible, or at least it is very difficult, to remove the cover 230 from the cap 205 without breaking it). At the same time, the ribs 319 and 535 slot in, so as to prevent any relative rotation of the cover 230 and the cap 205.

Figure 6C:
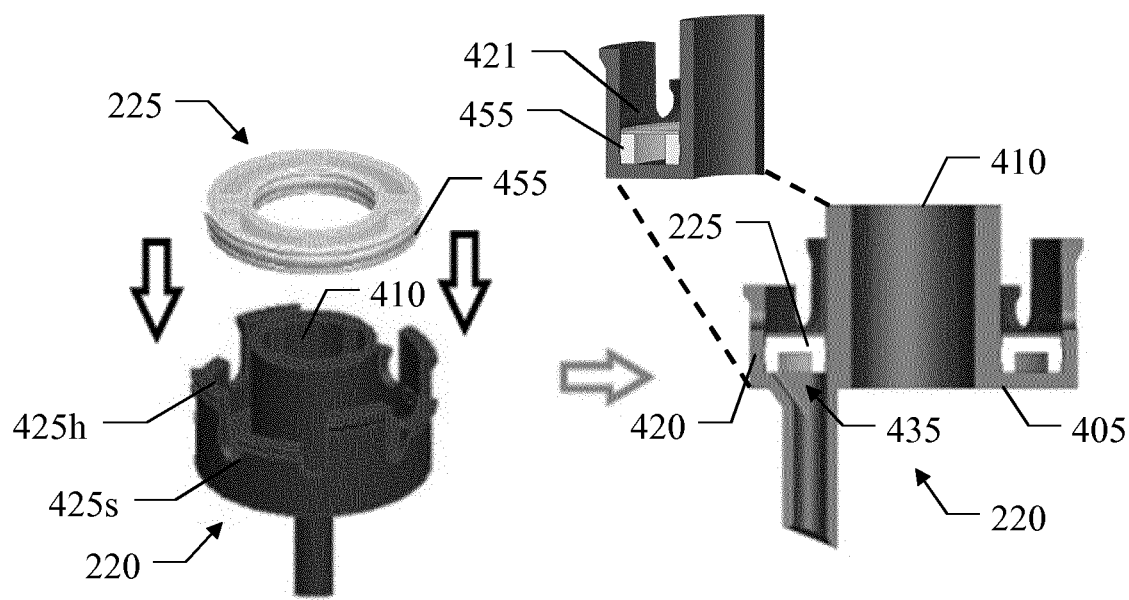

Moving to FIG. 6C, before, concurrently or after the above-mentioned operations, the filter 225 is mounted into the slider 220 by pushing it (from above, as indicated by the arrows) into the region comprised between the turret 410 and the tabs 425h, 425s. The filter 225 is pushed until it abuts against the disk 405 of the slider 220. As a result, the filter 225 is housed into the seat 435 of the slider 220 (between the turret 410 and the crown 420 thereof); as better visible in a corresponding enlarged portion of the slider 220 and the filter 225, at the same time, the bulging lateral wall 455 of the filter 225 and the bumps 421 of the slider 220 retain the filter 225 in place during the next handling of the slider 220.

Figure 6D:
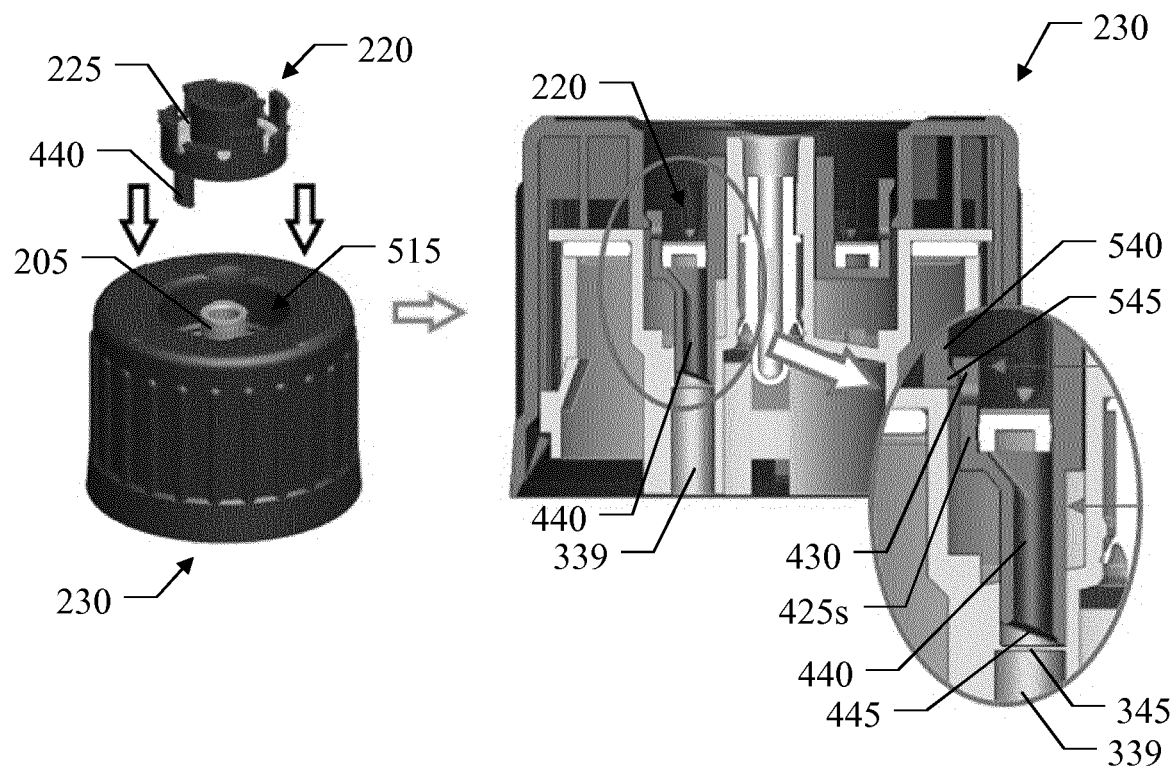

Moving to FIG. 6D, the slider 220 (already provided with the filter 225) is mounted into the cover 230 (already provided with the cap 205) by pushing it (from above, as indicated by the arrows) within the through-hole 515 of the cover 230, with the slider suction conduit 440 forward-facing (downwards) and aligned with the cap suction conduit 339. The slider 220 is pushed downwards until the teeth 430 of its shorter tabs 425s engage with the lip 545 of the crown 540 of the cover 230. As a result, the slider suction conduit 440 enters the cap suction conduit 339, but to an extent that the sharpened tip 445 of the slider suction conduit 440 does not reach (and thus does not break) the frangible element 345.

Figure 6E:
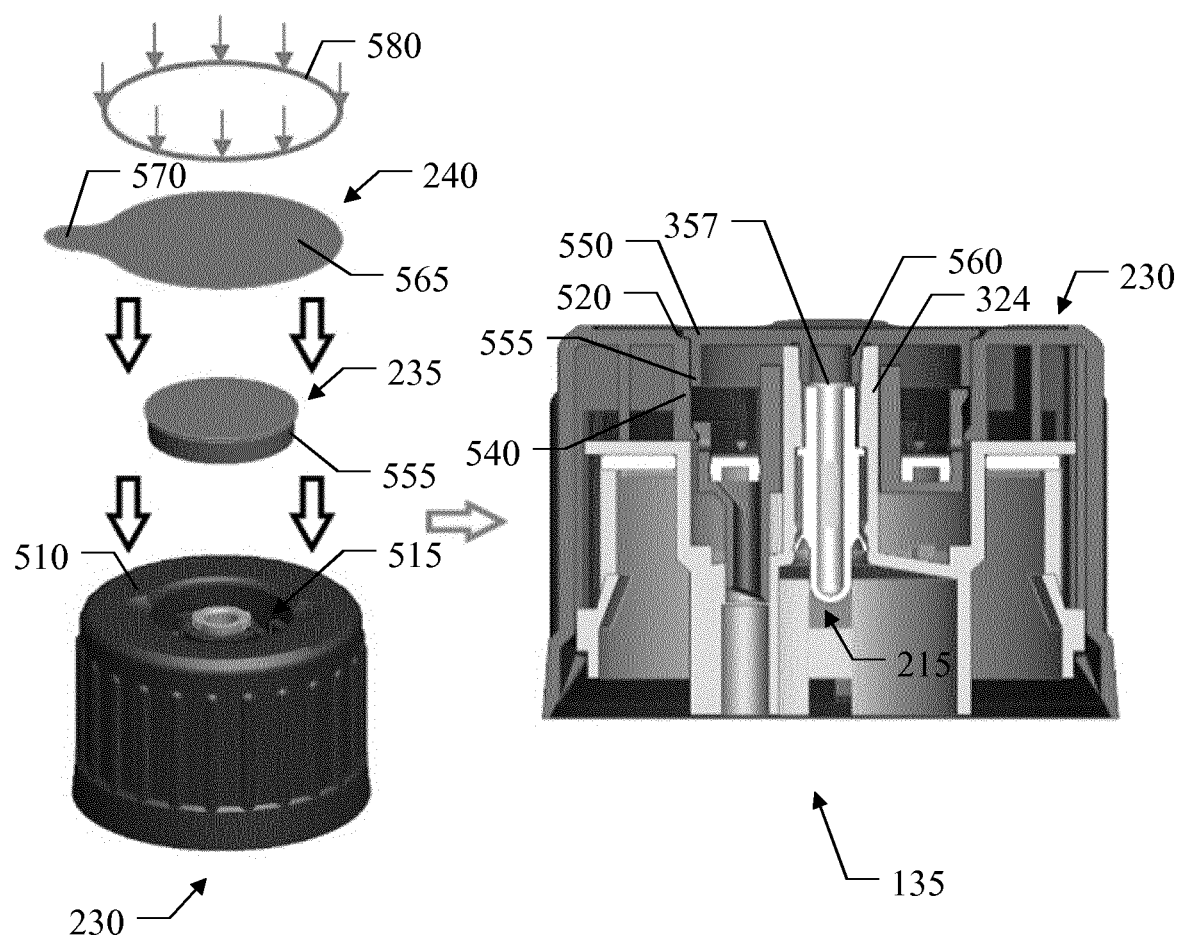

Moving to FIG. 6E, the lid 235 is mounted into the cover 230 (already provided with all the above-mentioned components) by pushing it (from above, as indicated by the arrows) into the through-hole 515, with its crown 555 forward-facing (downwards). The lid 235 is pushed until the disk 550 abuts against the counterbore 520 of the cover 230. As a result, the crown 555 and the turret 560 of the lid 235 are press-fitted into the crown 540 and into the delivery conduit 324, respectively (with their interference that retains the lid 235 in place). In this condition, the free end of the turret 560 (i.e., the extremity that is not connected to the disk 550) is positioned slightly above (i.e., not in contact with) the open end 357 of the valve member 215. At this point, the protection film 240 is placed over the cover 230, with its circular body 565 positioned around the through-hole 515 (thereby covering the lid 235) and its handling tab 570 slightly and freely projecting outside the disk 510 of the cover 230. The protection film 240 is welded (i.e., heat sealed) or glued to the disk 510 along a border of the circular body 565, so as to complete the closure 135. Reference 580 shows an example of distribution of welded joints at the peripheral border of the protection film 240 in order to associate the latter with the disk 510 of the cover 230. In this way, the protection film 240 is attached to the cover 230 in a peelable way (i.e., so as to be easily detachable by the user's hands without requiring any tool).

In view of the above, the closure may be assembled automatically and then at low cost. Moreover, all the components of the closure of the present disclosure may be easily associated by means of a pushing force, fact which advantageously simplifies its manufacturing.

Figure 7:
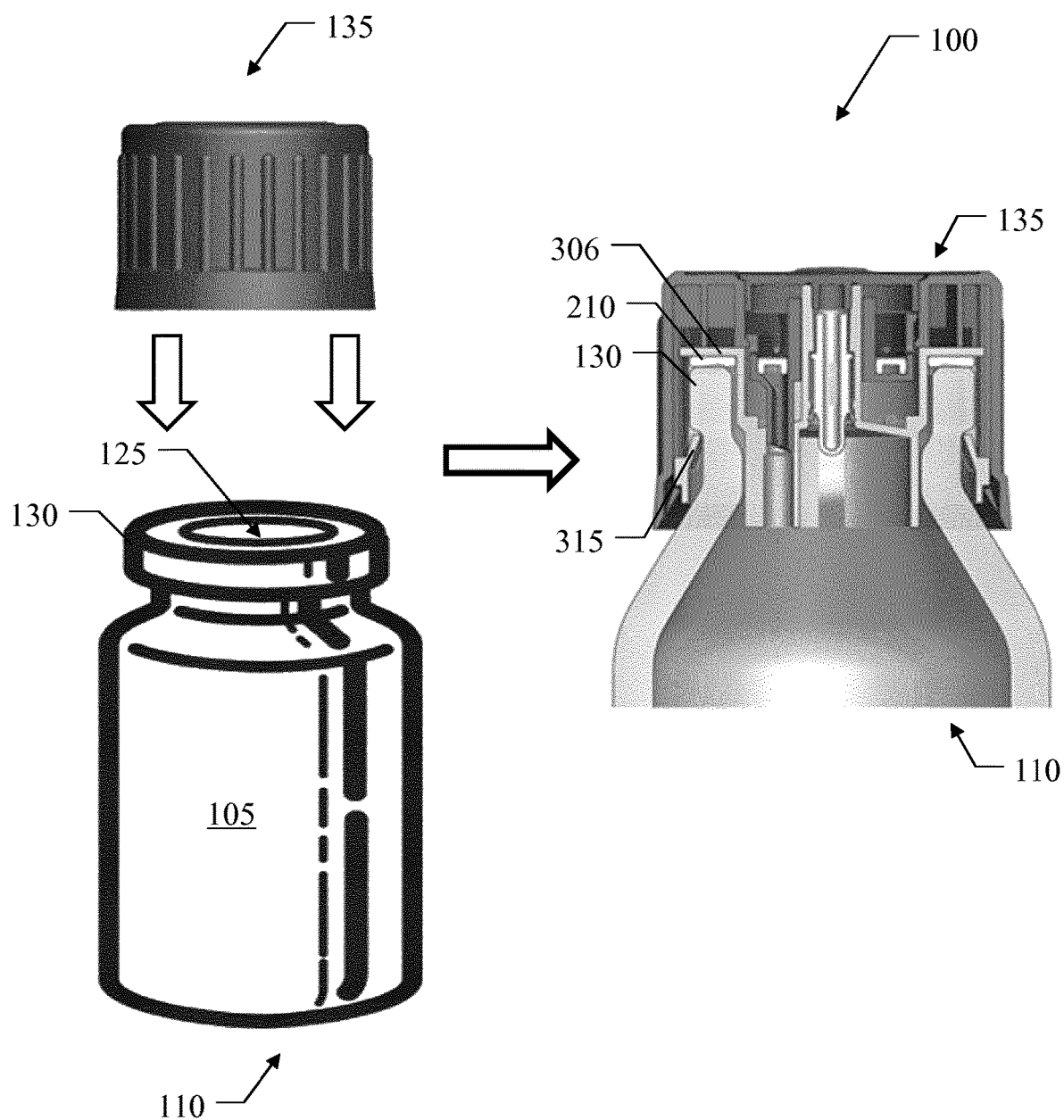
FIG. 7 shows the main steps of a process for manufacturing the medical product according to an embodiment of the present disclosure.

With reference now to FIG. 7, the main steps are shown of a process for manufacturing the medical product 100 according to an embodiment of the present disclosure.

The container 110 is filled through its mouth 125 with the medical liquid 105. At this point, the closure 135 (possibly after a preliminary sterilization thereof) is snap fitted onto the container 110 by pushing it (from above, as indicated by the arrows) onto the mouth 125, with its open end forward-facing (downwards). When the teeth 315 of the closure 135 engage the rim 130 of the container 110, the inwards orientation of the teeth 315 causes their resilient yielding, thereby allowing the closure 135 to pass over the rim 130 and to fix to the container 110 (with the teeth 315 that then return elastically to their original position as soon as the rim 130 has been overcome, thereby guaranteeing the necessary grip force). The closure 135 is pushed until the disk 306 abuts against an edge of the mouth 125, through the gasket 210 compressed between them. As a result, when the pushing force onto the closure 135 is released, the gasket 210 elastically tends to return to its original shape. In this way, the gasket 210 pushes the closure 135 away from the container 110 (upwards) and, as a result thereof, the teeth 315 are forced against an undercut of the rim 130, and thus the closure 135 is firmly fixed to the container 110. Moreover, since the teeth 315 are not accessible from the outside of the closure 135, the fixing is non-reversible (i.e., it is not possible, or at least it is very difficult, to remove the closure 135 from the container 110 without breaking it). This prevents (or at least substantially hinders) any tampering of the medical product 100. Indeed, the closure 135 may be detached from the container 110 only by breaking the closure 135 itself and thus rendering the latter unsuitable for a successive use. This aspect clearly improves the safety of the medical product 100. At the same time, the (at least partially compressed) gasket 210 seals the container 110 from the external environment.

The medical product 100 is then sterilized in an autoclave (not shown in the figure). The closure 135 is configured (for example, according to the rigidity of the teeth 315) so as to ensure its fixing to the container 110 during this sterilization phase, especially during a warming transient thereof (wherein a relatively high pressure is created inside the container 110, not compensated yet by pressurized air injected into the autoclave).

In view of the above, the medical product may be assembled automatically and then at low cost. Moreover, the closure of the present disclosure may be easily associated with the container by means of a pushing force, fact which advantageously simplifies the manufacturing of the final medical product. The closure of the present disclosure may also be mounted onto any standard container made from any material, without requiring any specific modification of the container itself (for example, of its neck provided that it is sufficiently rigid for allowing a correct coupling with the closure).

With reference now to FIG. 8A-FIG. 8F, the main steps are shown of a process for using the medical product according to an embodiment of the present disclosure.

Figure 8A:
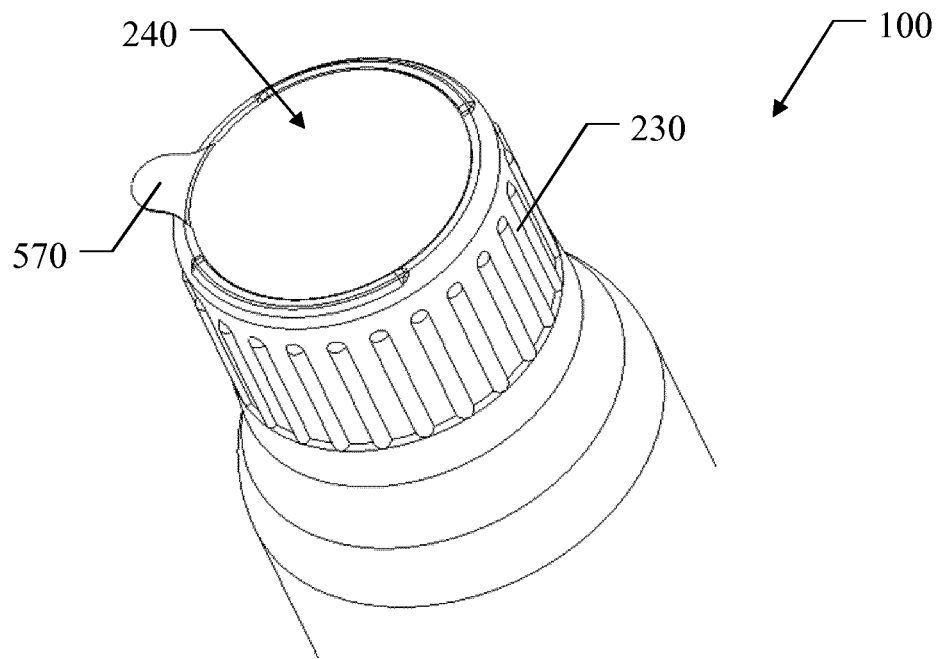
FIG. 8A-FIG. 8F show the main steps of a process for using the medical product according to an embodiment of the present disclosure.

Starting from FIG. 8A, when the medical product 100 has to be used (for example, to perform an injection as part of a CT scan examination of a patient), the operator, such as a healthcare assistant, at first removes the protection film 240. For this purpose, the operator grasps the handling tab 570 freely projecting outside the cover 230; the operator then pulls the handling tab 570 away from the cover 230 (in opposition to its welding thereto) so as to peel off the protection film 240.

Figure 8B:
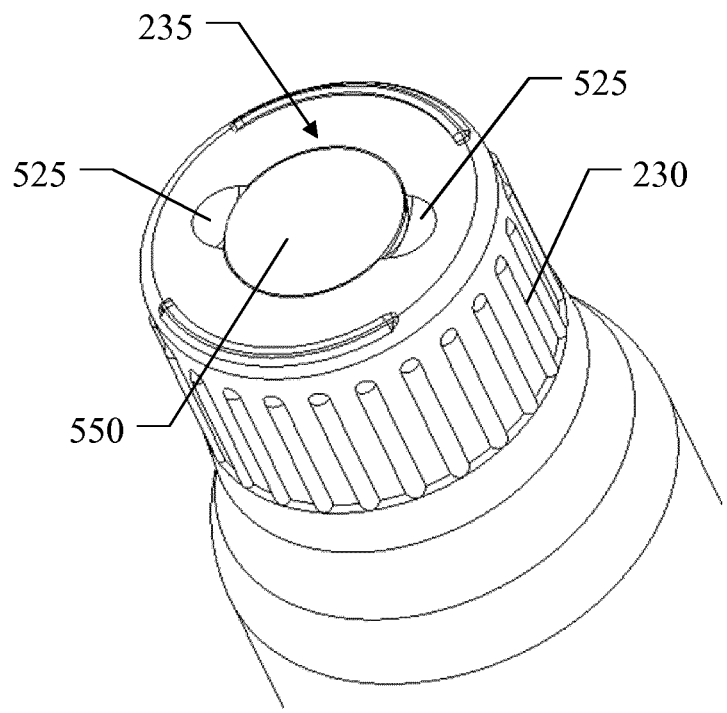

Moving to FIG. 8B, the operator removes the lid 235. For this purpose, the operator pinches the disk 550 by inserting the tips of two fingers into the access dips 525; the operator then pulls the disk 550 away from the cover 230 (in opposition to its press-fitting therein) so as to detach the lid 235 from the cover 230.

Figure 8C:
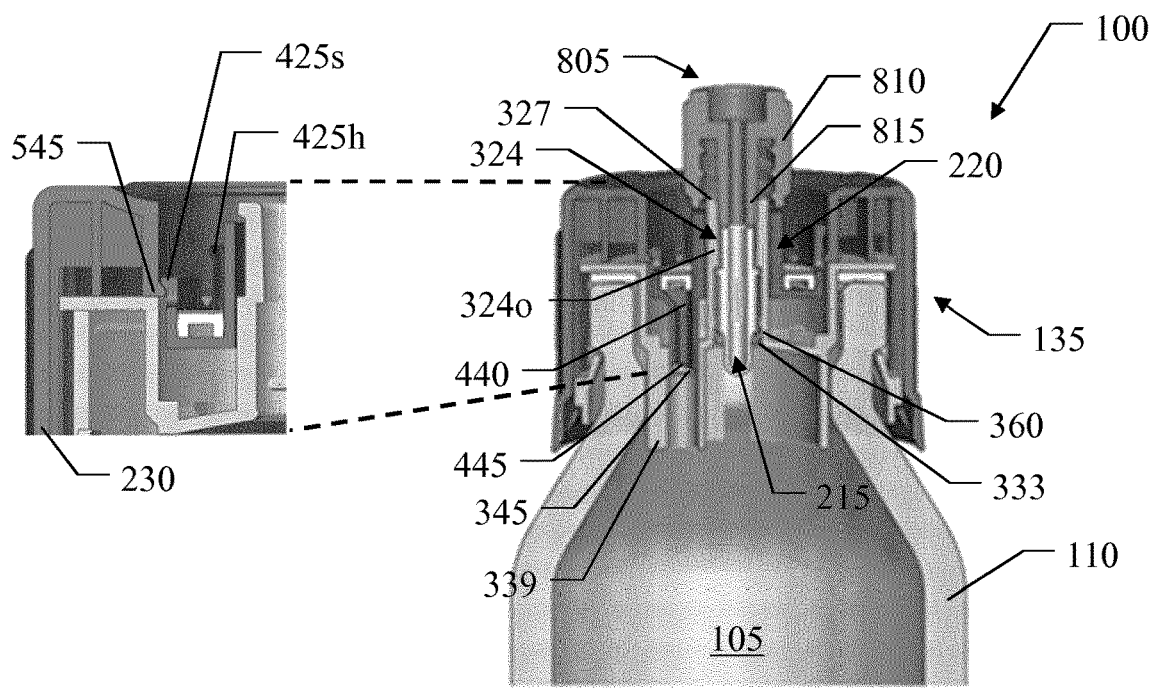

Moving to FIG. 8C, the operator connects the medical product 100 to the delivery device (not shown in the figure).

For example, the delivery device may be a syringe to be filled with the medical liquid 105 present in the container 110. Typically, the syringe is a needle-less syringe having a tip provided with a connector that suitably matches and engages the connector 327 of the closure 135. Preferably, the syringe (once it has been filled with the medical liquid 105) becomes a pre-filled syringe that is used in syringe injectors (for example, Empower CTA or Empower CTA+ manufactured by Bracco Injeneering SA, trademarks) for injecting a contrast agent, a saline solution, a therapeutic substance (for example, a drug) and/or a combination thereof during a diagnostic procedure (for example, a CT, MR or ultrasound imaging applications) or a therapeutic infusion. Alternatively, the delivery device may be a syringe-less injector (for example, CT Exprés manufactured by Bracco Injeneering SA, trademarks). In particular, the connector 327 may be engaged by a connector provided at a free end of a transfer line, which connects a supply station to a pressurizing unit (for example, a peristaltic pump) of the injector. The supply station (typically from two to three for each injector) comprises a container (a bottle or a bag) for supplying the medical liquid (for example, contrast agent, saline or a combination thereof) to be injected into a patient during a scan examination (for example, a CT imaging procedure). A transfer line is typically provided for each supply station and the set (i.e., the totality) of the various transfer lines defines a delivery arrangement, which is often indicated by the technicians as "Day Set" or "Transfer Set". The closure according to the present disclosure may be advantageously used for directly connecting the container of the medical liquid with a transfer line of the delivery arrangement, thereby simplifying some preparatory steps for executing the injection as well as reducing some risks associated therewith. For instance, by using the closure of the present disclosure it is possible to avoid a specific and additional bottle connector which is typically used for connecting the bottle of a supply station to a transfer line, said bottle connector comprising a spike that pierces a rubber membrane of the bottle cap for accessing the liquid contained within the bottle. It is apparent that eliminating a component, as well as all the necessary operation steps needed for its connection, and, even more, avoiding the use of a piercing element, contributes in increasing the safety of the injector (for example, reducing the risk of environment contamination), in increasing the safety of the operator (who any longer does not run the risk of injuring himself) and in reducing the overall cost of a single injection procedure.

In any case, whatever it is, the injection system is typically provided with a connector 805 mating the connector 327 of the closure 135. For example, the connector 805 is a male luer lock fitting comprising a sleeve 810 that is provided with an internal thread matching the external thread possessed by the connector 327. The male luer lock fitting 805 further comprises a (tapered) connection conduit 815 housed within the sleeve 810, an outside surface of the connection conduit 815 matching the inside surface of the outer portion 324o of the delivery conduit 324. The operator fits the connector 805 onto the connector 327 (i.e., the operator introduces a free end of the connection conduit 815 into a front part of the outer portion 324o of the delivery conduit 324) and then s/he screws the connector 805 onto the connector 327 (alternatively, the operator screws the connector 327 onto the connector 805). As a result, the connector 805 rotationally slides (i.e., translates) into the container 110 (downwards).

As soon as the free end of the connection conduit 815 reaches the valve member 215, the connection conduit 815 pushes the valve member 215 inwards the container 110. A resulting force that is exerted by the connection conduit 815 on the valve member 215 causes the resilient yielding of the skirt 360, thereby allowing it to pass over the humps 333, with the skirt 360 that soon after elastically returns to its original position (see FIG. 8D). At the same time, the sleeve 810 pushes the slider 220 inwards the container 110. The same force that is exerted by the sleeve 810 on the slider 220, as better visible in a corresponding enlarged portion of the slider 220 and the cover 230, causes the resilient yielding of its shorter tabs 425s, thereby allowing them to pass over the lip 545 of the cover 230 (with the shorter tabs 425s that then elastically return to their original position). The slider suction conduit 440 then slides accordingly (downwards) along the cap suction conduit 339. As soon as the sharpened tip 445 of the slider suction conduit 440 reaches the frangible element 345, the sharpened tip 445 breaks the frangible element 345 (see FIG. 8D); the configuration of the sharpened tip 445 facilitates the breaking of the frangible element 345, without any risk of detachment of particles thereof. The (broken) frangible element 345 remains attached to the border of the cap suction conduit 339, housed into a corresponding notch formed therein (not shown in the figure), so as to remain adherent to the cap suction conduit 339 thereby avoiding any risk of blocking the passage of the air. As better visible in the same enlarged portion of the slider 220 and the cover 230 of above, when the higher tabs 425*h* of the slider 220 reach the lip 545, the same force that is exerted by the sleeve 810 onto the slider 220 likewise causes the resilient yielding of the higher tabs 425*h*, thereby allowing them to pass over the lip 545, with the higher tabs 425*h* that then elastically return to their original position (see FIG. 8D).

Figure 8D:
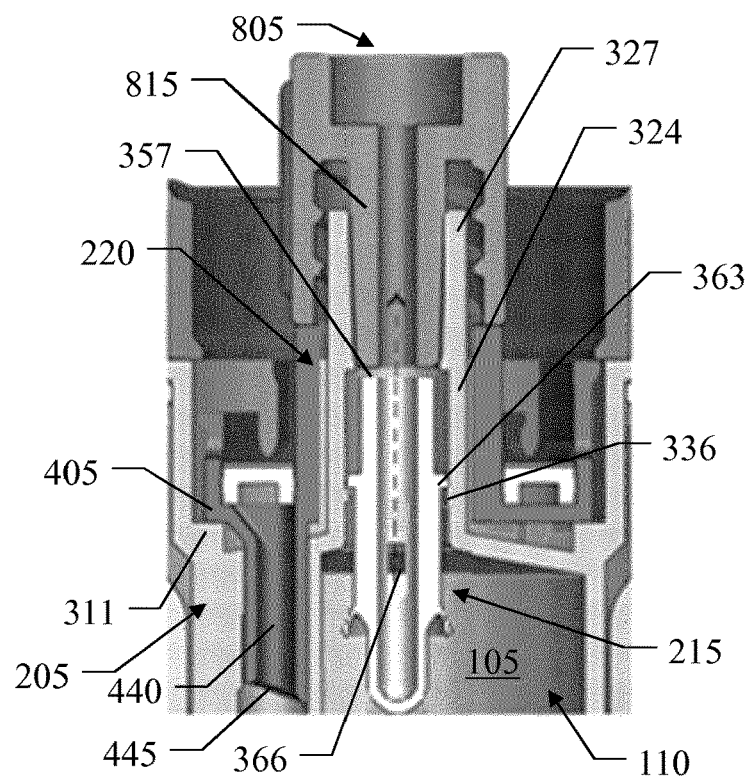

As shown in FIG. 8D, the connector 805 is screwed onto the connector 327 until the disk 405 of the slider 220 abuts against the bottom wall 311 of the cap 205 (thereby ceasing pushing the valve member 215 and the slider 220). At this point of the operation, the valve member 215 is brought to an open position, wherein the windows 366 project (at least in part) from the delivery conduit 324 into the container 110 (i.e., the windows 366 are at least partially exposed inside the container 110), so as to put the windows 366 in fluid communication with the interior of the container 110 (therefore allowing the medical liquid 105 to reach the windows 366 and to pass through them). Moreover, the mechanical interference of the open end 357 of the valve member 215 with the delivery conduit 815 of the connector 805 and the mechanical interference of the rim 363 with the steps 336 of the delivery conduit 324 retain the valve member 215 correctly in place. In particular, the steps 336 prevent the valve member 215 from falling down into the container 110. Moreover, the substantial mechanical alignment between the open end 357 of the valve member 215 and the delivery conduit 815 of the connector 805 forms a fluid path between them. It is pointed out that in order to guarantee this suitable fluid communication there is no need that the open end 357 of the valve member 215 mechanically interferes (i.e., touches) the delivery conduit 815 of the connector 805. Therefore, by screwing the connector 805 onto the connector 327, two simultaneous operations are performed, i.e., the valve member 215 is brought to the open position and the sharpened tip 445 of the slider suction conduit 440 reaches and breaks the frangible element (not visible in the figure) for allowing the air to enter the container 110.

Figure 8E:
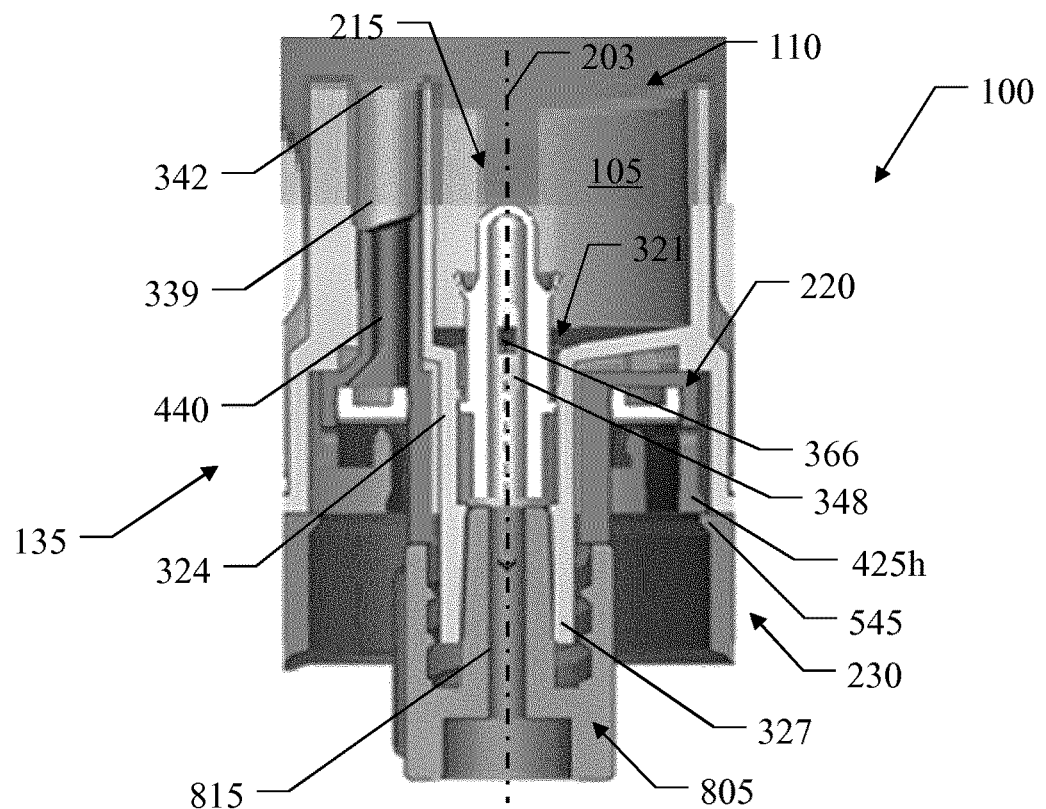

Moving to FIG. 8E, the operator overturns the medical product 100 in order to have the closure 135 facing downwards (with the connection conduit 815 of the connector 805 that prevents the valve member 215, and then its windows 366, to re-enter the delivery conduit 324). In this condition, the medical liquid 105 flows from the container 110 through the windows 366 into the tube 348 of the valve member 215 and then into the connection conduit 815 of the connector 805. At the same time, air is suctioned from the external environment through the slider suction conduit 440 and the cap suction conduit 339, and then it enters the container 110 through the suction port 342. The air entering the container 110 compensates for the pressure reduction within the container 110 caused by the delivery of the medical liquid 105 (balancing an internal pressure in the container 110 with an atmospheric pressure outside it). Moreover, thanks to the design of the closure 135 (especially thanks to the fact that the delivery port 321 is spaced apart along the longitudinal axis 203 of the closure 135 from the suction port 342, i.e., the two ports are at different heights—different depths—inside the container 110), the air enters the container 110 far away from the delivery port 321 (from which the medical liquid 105 exits the container 110), so as to significantly limit any risk of mixing air bubbles with the medical liquid 105 that is delivered from the container.

Once the desired operation has been completed (for example, the container 110 has been emptied, or one or more injections associated with scan examinations have been completed), the operator unscrews the connector 805 from the connector 327 (either in this overturned condition or after the medical product 100 has been overturned again to have the closure 135 facing upwards). In any case, even if the connector 805 is removed from the closure 135 when it is facing downwards, the slider 220 is prevented from falling down thanks to the higher tabs 425*h* that engage and are supported by the lip 545 of the cover 230.

Figure 8F:
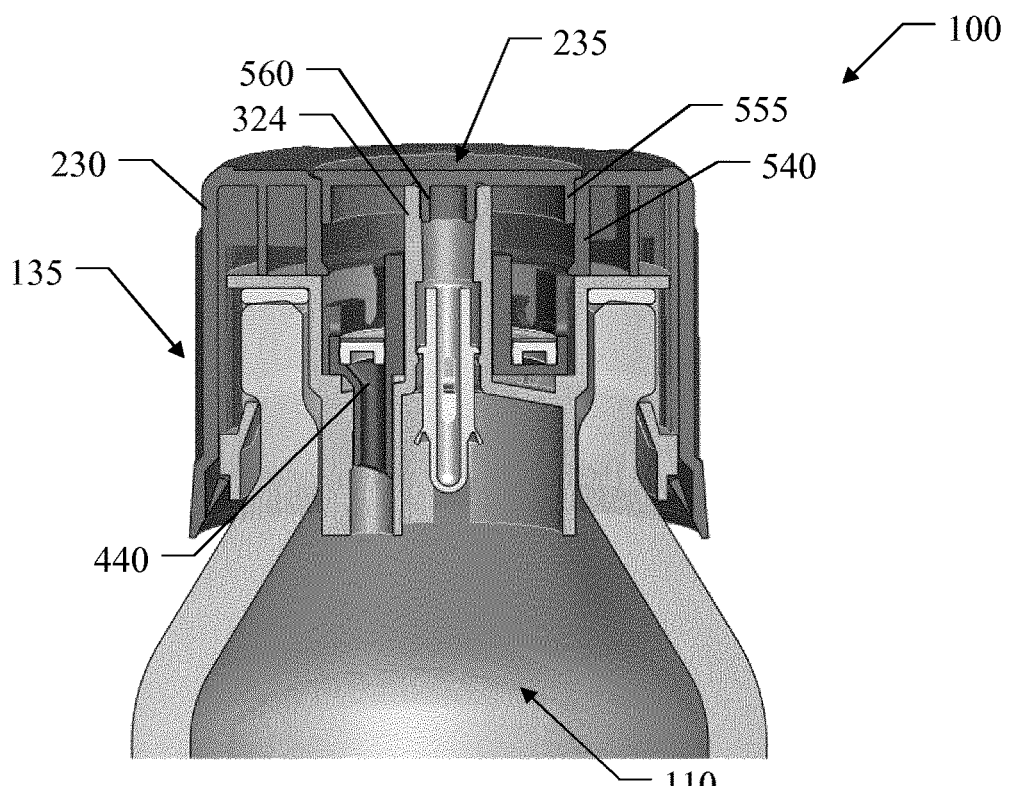

Moving to FIG. 8F, finally the operator overturns the medical product 100 again to have the closure 135 facing upwards (if not already done before). The operator then mounts the lid 235 onto the cover 230 so as to have the crown 555 and the turret 560 press-fitted into the crown 540 and into the delivery conduit 324, respectively (with their interference that retains the lid 235 in place during the next handling of the medical product 100). In this way, the lid 235 closes the delivery conduit 324 and the slider suction conduit 440, so as to prevent the dispersion of any medical liquid that may have remained inside the container 110. The operator then disposes the (substantially empty) medical product 100 as usual.

MODIFICATIONS

In order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof; conversely, well-known features may have been omitted or simplified in order not to obscure the description with unnecessary particulars. Moreover, it is expressly intended that specific elements and/or method steps described in connection with any embodiment of the present disclosure may be incorporated in any other embodiment as a matter of general design choice. In any case, each numerical value should be read as modified by the term about (unless already done) and each range of numerical values should be intended as expressly specifying any possible number along the continuum within the range (comprising its end points). Moreover, ordinal or other qualifiers are merely used as labels to distinguish elements with the same name but do not by themselves connote any priority, precedence or order. The terms include, comprise, have, contain and involve (and any forms thereof) should be intended with an open, non-exhaustive meaning (i.e., not limited to the recited items); the terms based on, dependent on, according to, function of (and any forms thereof) should be intended as a non-exclusive relationship (i.e., with possible further variables involved); the term a/an should be intended as one or more items (unless expressly indicated otherwise); and the term means for (or any means-plus-function formulation) should be intended as any structure adapted or configured for carrying out the relevant function.

For example, an embodiment provides a closure for closing a mouth of a container of a liquid. However, the closure may be of any type, shape, size and material, and it may be used with any container of any liquid (see below).

In an embodiment, the closure comprises a cap. However, the cap may be of any type, shape, size and material.

In an embodiment, the cap has fixing means for fixing the cap to the container. However, the fixing means may be implemented with any structure (for example, in addition to the above-described teeth of the cap, the fixing means may be of any other snap-fitting type, or of any screwing type).

In an embodiment, the cap has a delivery port for delivering the liquid from the container. However, the delivery port may be of any shape, size and it may be provided at any suitable position within the closure.

In an embodiment, the cap has a valve member in a closed position wherein the valve member closes the delivery port. However, the valve member may be of any type, shape, size and material (for example, a tube, a disc, a ball) and it may close the delivery port in any way (for example, spaced apart from the delivery port or arranged at a border thereof).

In an embodiment, the cap has a cap suction conduit for suctioning air into the container during the delivering of the liquid. However, the cap suction conduit may be of any shape, size and it may be provided at any suitable position within the closure.

In an embodiment, the cap has a connector for connecting to a delivery device of the liquid, which connector is in fluid communication with the delivery port. However, the connector may be of any type, shape, size and at any position (for example, of locking or fitting type, male or female), for connecting to any delivery device (for example, of an injection system or a syringe) in any way (for example, by screwing, snap-fitting the delivery device and/or the connector); moreover, the connector may be in fluid communication with the delivery port in any way (for example, via the delivery conduit as described above, via any other element or even directly).

In an embodiment, the closure comprises a slider. However, the slider may be of any type, shape, size and material.

In an embodiment, the slider is slidebly coupled with the cap. However, the slider may be coupled with the cap in any way (for example, with one or more rails).

In an embodiment, the slider has a slider suction conduit for suctioning the air into the container during the delivering of the liquid, which slider suction conduit is slidebly coupled with the cap suction conduit. However, the slider suction conduit may be of any shape, size and at any position; moreover, the slider suction conduit may slide with respect to the cap suction conduit in any way (for example, internally as described above or externally should the frangible element be provided in the slider suction conduit) and to any extent (up to completely, always or only for breaking the frangible element), and it may be at any position with respect to the frangible element (for example, with or without a dedicated system for maintaining them spaced apart).

In an embodiment, the closure comprises a frangible element closing the cap suction conduit or the slider suction conduit. However, the frangible element may be of any type, shape, size and material (for example, a membrane, a septum, a thin wall, with or without any feature for facilitating its breaking, such as pre-cut lines extending in any direction, like circumferentially or radially, and/or thinner portions); moreover, the frangible element may be at any position (for example, in the cap suction conduit as described above or in the slider suction conduit if the cap suction conduit slides inside it, at any position in the corresponding suction conduit, either within it or at its border, with the other suction conduit at any distance thereof).

In an embodiment, the closure is configured to cause the delivery device during the connecting thereof to move inwards the container (in a fixed condition wherein the closure is fixed to the container). However, this result may be achieved in any way (for example, by screwing or pushing the delivery device).

In an embodiment, the delivery device thus moves the valve member inwards the container to an open position (wherein the valve member opens the delivery port) and moves the slider inwards the container to break the frangible element (thereby putting the slider suction conduit in fluid communication with the cap suction conduit). However, the delivery device may act in any way (for example, at one or more points) to open the valve in any way (for example, by translating and/or rotating it) and to break the frangible element in any way (for example, centrally, laterally); moreover, additional operations may be performed at the same time (for example, breaking a further frangible element closing the delivery port, opening the valve member in opposition to an elastic element that biases it to return closed as soon as the delivery device is removed).

In an embodiment, the fixing means are for fixing the cap to the container in a non-removable way. However, this result may be achieved in any way (for example, with any snap-fitting structure, such as with any number of teeth, with an external fastener, such as a band); in any way, the possibility is not excluded of having the cap removable (more or less easily).

In an embodiment, the closure comprises a cover that is fixed in a non-removable way to the cap. However, the cover may be of any type, shape, size, material and it may be fixed to the cap in any way (either the same or different with respect to the fixing of the cap to the container, even in a removable way); in any case, the cover may also be omitted at all.

In an embodiment, the cover prevents access to the fixing means (in the fixed condition of the closure). However, the cover may have any function (comprising a mere aesthetic one).

In an embodiment, the cap has an external structure and the cover has an internal structure interfering with the external structure for preventing a mutual rotation of the cover and the cap around a longitudinal axis of the closure. However, this result may be achieved in any way (for example, with the above-described staggered ribs, with teeth); in any case, the possibility is not excluded of leaving the cover and the cap free to rotate reciprocally.

In an embodiment, the cap suction conduit has a suction port at an end thereof opposite the slider suction conduit. However, the suction port may have any shape and size, and it may be arranged at any position within the container (for example, facing inwards, laterally).

In an embodiment, the delivery port and the suction port are spaced apart along a longitudinal axis of the closure. However, the delivery port and the suction port may be at any relative position (for example, with the delivery port more internal or more external than the suction port with respect to the container in the fixed condition of the closure); in any case, the delivery port and the suction port may be at any distance longitudinally (down to zero).

In an embodiment, the cap comprises a delivery conduit (connecting the delivery port and the connector). However, the delivery conduit may be of any shape, size and at any position (for example, central, peripheral).

In an embodiment, the slider comprises a through-hole for sliding along the delivery conduit. However, the slider may be coupled with the delivery conduit in any way (for example, completely or partially surrounding it).

In an embodiment, the connector is configured to cause a sleeve of the delivery device to slide outside the delivery conduit for moving the slider (during the connecting of the delivery device). However, the sleeve may be of any shape, size and at any position; in any case, the delivery device may act on the slider in any other way (for example, through a pin, a tab).

In an embodiment, the connector is configured to cause a connection conduit of the delivery device to slide inside the delivery conduit for moving the valve member (during the connecting of the delivery device). However, the connection conduit may be of any shape, size and at any position; in any case, the delivery device may act on the valve member in any other way (either the same or different with respect to the slider, independently or together).

In an embodiment, the delivery conduit has an external thread matching an internal thread of the sleeve for screwing the delivery device during the connecting thereof (and thus causing the delivery device to move inwards the container in the fixed condition). However, the threads may be of any type, shape, size and at any position (for example, with the sleeve that is screwed inside the delivery conduit).

In an embodiment, the valve member comprises a tube with a lateral wall. However, the tube may be of any shape and size.

In an embodiment, the tube has a closed end and an open end that face inwards and outwards, respectively, the container in the fixed condition of the closure (with the open end that is arranged inside the delivery conduit). However, the closed end and the open end may be of any type (for example, a rounded or flat closed end, a total or partial open end).

In an embodiment, the tube has one or more windows that are opened in the lateral wall (with the windows that are arranged inside the delivery conduit in the closed position of the valve member and are arranged at least in part outside the delivery conduit in the open position of the valve member). However, the windows may be in any number, of any shape, size and at any position; moreover, the windows may be arranged completely or only in part outside the delivery conduit to open the delivery port.

In an embodiment, the closure comprises first valve stopping means for maintaining the valve member in the closed position (with the delivery device that moves the valve member to the open position by overcoming the first valve stopping means). However, the first valve stopping means may be implemented with any structure (for example, by the above-mentioned humps of the cap in combination with the skirt of the valve member, by one or more teeth, arranged on the valve member and/or on the cap) or they may be omitted at all (for example, by simply exploiting a friction between the valve member and the cap).

In an embodiment, the closure comprises second valve stopping means for preventing the valve member to leave the cap when the valve member is in the open position. However, the second valve stopping means may be implemented with any structure, either the same or different with respect to the first valve stopping means, independently or together (for example, the above-described steps of the cap in combination with the rim of the valve member, one or more teeth arranged on the valve member and/or on the cap) or they may be omitted at all (for example, by simply exploiting a friction between the valve member and the cap in this case as well).

In an embodiment, the slider suction conduit ends with a sharpened tip facing the cap suction conduit for facilitating the breaking of the frangible element. However, the sharpened tip may be of any type (for example, a slanted end or a needle); in any case, the slider suction conduit may end with any other shape.

In an embodiment, the closure comprises first slider stopping means for maintaining the slider suction conduit spaced apart from the frangible element (with the delivery device that moves the slider by overcoming the first slider stopping means). However, the first slider stopping means may be implemented with any structure (for example, the above-mentioned lower tabs of the slider in combination with the lip of the cover, a skirt arranged on the slider, the cap and/or the cover) or they may be omitted at all (for example, by simply exploiting a friction between the slider and the cap).

In an embodiment, the closure comprises second slider stopping means for preventing the slider to leave the cap after breaking the frangible element. However, the second slider stopping means may be implemented with any structure, either the same or different with respect to the first slider stopping means, independently or together (for example, the above-mentioned higher tabs of the slider in combination with the lip of the cover, one or more teeth arranged on the slider, the cap and/or the cover) or they may be omitted at all (for example, by simply exploiting a friction between the slider and the cap in this case as well).

In an embodiment, the closure has a further through-hole that exposes the connector and the slider suction conduit. However, the further through-hole may be of any shape, size and at any position (for example, with or without any access dips). In an embodiment, the closure comprises a press-fitting lid closing the further through-hole. However, the lid may be of any shape, size, material, and it may be fixed in any way (for example, by snap fitting or screwing); in any case, the lid may also be omitted at all (for example, to avoid closing the container in order to prevent any further use thereof so that each container is used for one single patient only and it may not be re-used for more patients).

In an embodiment, the closure comprises a peelable protection film that seals the further through-hole (closed by the lid). However, the protection film may be of any shape, size, material (for example, with or without the handling tab), and it may be fixed in any way (for example, welded or glued); in any case, the protection film may also be omitted at all (either alone or together with the lid).

In an embodiment, the closure comprises a filter for filtering the air that is suctioned through the slider suction conduit. However, the filter may be of any type (for example, one or more membranes or spongy layers for filtering bacteria, other microorganisms, dust), or it may be omitted at all.

In an embodiment, the filter has an extent higher than a cross-section of the cap suction conduit. However, the filter may be of any shape, size and at any position (for example, only around the suction port); in any case, the possibility is not excluded of using a filter matching the cap suction conduit only.

An embodiment provides a product that comprises a container containing a liquid and the above-mentioned closure fixed to the container (to close a mouth thereof). However, the product may be of any type (for example, for medical or non-medical applications). The container may be of any type (for example, a bottle, a vial or any other container with a rigid mouth) and of any size, shape and material (for example, glass, plastic); the container may contain any amount and type of liquid (for example, in medical applications for diagnostic or therapeutic purposes, the liquid may be a contrast agent, a saline solution, a drug, or more generally in non-medical applications for any other purpose, the liquid may be, for example, polish, enamel, varnish, dye).

Generally, similar considerations apply if the closure and the product comprising it each one has a different structure or comprises equivalent components (for example, of different materials), or it has other operative characteristics. In any case, every component thereof may be separated into more elements, or two or more components may be combined together into a single element; moreover, each component may be replicated to support the execution of the corresponding operations in parallel. Moreover, unless specified otherwise, any interaction between different components generally does not need to be continuous, and it may be either direct or indirect through one or more intermediaries.

An embodiment provides a method for using the above-mentioned product, which method comprises connecting a delivery device to the closure, the delivery device during the connecting thereof moving the valve member to open the delivery port and moving the slider to break the frangible element (thereby putting the slider suction conduit in fluid communication with the cap suction conduit).

An embodiment provides a method for assembling the above-mentioned closure, which method comprises mounting the slider into the cap. However, the result may be achieved in different ways (for example, by inserting the gasket and the valve member into the cap after it has been inserted into the cover).

An embodiment provides a method for manufacturing the above-mentioned product, which method comprises filling the container with the liquid and then mounting the closure onto the container.

Generally, similar considerations apply if the same solution is implemented with equivalent methods (by using similar steps with the same functions of more steps or portions thereof, removing some steps being non-essential, or adding further optional steps); moreover, the steps may be performed in a different order, concurrently or in an interleaved way (at least in part).

The invention claimed is:

1. A closure (135) for closing a mouth (25) of a container (110) of a liquid (105), the closure (135) comprising:
   a cap (205) having fixing means (315) for fixing the cap (205) to the container (110), a delivery port (321) for delivering the liquid (105) from the container (110), a valve member (215) in a closed position wherein the valve member (215) closes the delivery port (321), a cap suction conduit (339) for suctioning air into the container (110) during the delivering of the liquid (105) and a connector (327) >for connecting to a delivery device (805) of the liquid (105), the connector (32) being in fluid communication with the delivery port (321),
   a slider (220) slidebly coupled with the cap (205), the slider (220) having a slider suction conduit (2140) for suctioning the air into the container (110) during the delivering of the liquid (105) slidebly coupled with the cap suction conduit (339), and
   a frangible element (345) closing the cap suction conduit (339) or the slider suction conduit (440),
   wherein the closure (135) is configured to cause the delivery device (805) during the connecting thereof to move inwards the container (110), in a fixed condition wherein the closure (135) is fixed to the container (110), and thus moving the valve member (215) inwards the container to an open position, wherein the valve member (215) opens the, delivery port (321), and moving the slider (220) inwards the container to break the frangible element (345), thereby putting in fluid communication the slider suction conduit (440) with the cap suction conduit (339).

2. The closure (135) according to claim 1, wherein the fixing means (315) are for fixing the cap (205) to the container (110) in a non-removable way and wherein the closure (135) comprises a cover (230) fixed in a non-removable way to the cap (205), the cover (230) preventing access to the fixing means (315) in the fixed condition of the closure (135).

3. The closure (135) according to claim 2, wherein the cap (205) has an external structure (319) and the cover (230) has an internal structure (535) interfering with the external structure (319) for preventing a. mutual rotation of the cover (230) and the cap (205) around a longitudinal axis (203) of the closure (135).

4. The closure (135) according to claim 1, wherein the cap suction conduit (339) has a suction port (342) at an end thereof opposite the slider suction conduit (440), the delivery port (321) and the suction port (342) being spaced, apart along a longitudinal axis (203) of the closure (135).

5. The closure (135) according to claim 1, wherein the cap (205) comprises a delivery conduit (324) connecting the delivery port (321) and the connector (327), the slider (220) comprising a through-hole (415) for sliding along the delivery conduit (324).

6. The closure (135) according to claim 5, wherein the connector (327) is configured to cause a sleeve (810) of the delivery device (805) to slide outside the delivery conduit (324) for moving the slider (220) and a connection conduit (815) of the delivery device (805) to slide inside the delivery conduit (324) tor moving the valve member (215) during the connecting of the delivery device (805).

7. The closure (135) according to claim 6, wherein the delivery conduit (324) has an external thread matching an internal thread of the sleeve (810) for screwing the delivery device (805) during the connecting thereof and thus causing the delivery device (805) to move inwards the container (110) in the fixed condition.

8. The closure (135) according to claim 5 wherein the valve member (215) comprises a tube (348) with a lateral wall (351), a closed end (354) and an open end (357) facing inwards and outwards, respectively, the container (110) in the fixed condition of the closure (135), the open end (357) being arranged inside the delivery conduit (324), and one or more windows (366) opened in the lateral wall (351), the windows (366) being arranged inside the delivery conduit (324) in the closed position of the valve member (215) and being arranged at least in part outside the delivery conduit (324) in the open position of the valve member (215).

9. The closure (135) according to claim 1, comprising first valve stopping means (333,360) for maintaining, the valve member (215) in the closed position, the delivery device (805) moving the valve member (215) to the open position by overcoming the first valve stopping means (333,360), and second valve stopping means (336,363) for preventing the valve member (215) to leave the cap (205) when the valve member (215) is in the Open position.

10. The closure (135) according to claim 1, wherein the slider suction conduit (440) ends with a sharpened tip (445) facing the cap suction conduit (339) for facilitating the breaking of the frangible element (345).

11. The closure (135) according to claim 1, comprising first slider stopping means (425s,545) for maintaining the slider suction conduit (440) spaced apart from the frangible element (345), the delivery device (805) moving the slider (220) by overcoming the first slider stopping means (425s, 545), and second slider stopping means (425h,545) for preventing the slider (220) to leave the cap (220) after breaking the frangible element (345).

12. The closure (135) according to claim 1, wherein the closure (135) has a further through-hole (515) exposing the connector (327) and the slider suction conduit (440), the closure (135) comprising a press-fitting lid (235) closing the further through-hole (515).

13. The closure (135) according to claim 12, comprising, a peelable protection film (240) sealing the further through-hole (515) closed by the lid (235).

14. The closure (135) according to claim 1, comprising a filter (225) for filtering the air being suctioned through the slider suction conduit (440), the filter (225) having an extent higher than a cross-section of the cap suction conduit (339).

15. A product (100) comprising a container (110) containing a liquid (105) and the closure (135) according to claim 1 fixed to the container (110) to close a mouth (125) thereof.

* * * * *

UNITED STATES PATENT AND TRADEMARK OFFICE
CERTIFICATE OF CORRECTION

PATENT NO. : 10,610,452 B2  
APPLICATION NO. : 16/474726  
DATED : April 7, 2020  
INVENTOR(S) : Anelli et al.

Page 1 of 1

It is certified that error appears in the above-identified patent and that said Letters Patent is hereby corrected as shown below:

In the Claims

Column 19, Line 42, Claim 1, "a mouth (25)" should read —a mouth (125)—.
Column 19, Line 51, Claim 1, "(327) >for connecting to" should read —(327) for connecting to—.
Column 19, Line 52, Claim 1, "the connector (32)" should read —the connector (327)—.
Column 19, Line 56, Claim 1, "conduit (2140) for" should read —conduit (440) for—.
Column 20, Line 1, Claim 1, "opens the, delivery port" should read —opens the delivery port—.
Column 20, Line 16, Claim 3, "preventing a. mutual rotation" should read —preventing a mutual rotation—.
Column 20, Line 22, Claim 4, "being spaced, apart" should read —being spaced apart—.
Column 20, Line 34, Claim 6, "conduit (324) tor moving" should read —conduit (324) for moving—.
Column 20, Line 42, Claim 8, "claim 5 wherein" should read —claim 5, wherein—.
Column 20, Line 54, Claim 9, "for maintaining, the" should read —for maintaining the—.
Column 20, Line 60, Claim 9, "in the Open position" should read —in the open position—.
Column 21, Lines 11-12, Claim 13, "claim 12, comprising, a" should read —claim 12, comprising a—.

Signed and Sealed this  
Eleventh Day of October, 2022

Katherine Kelly Vidal  
*Director of the United States Patent and Trademark Office*